United States Patent
Toman et al.

(10) Patent No.: US 6,472,171 B1
(45) Date of Patent: Oct. 29, 2002

(54) EXPRESSION OF PROCOLLAGEN IN YEAST

(75) Inventors: David P. Toman, Mountain View, CA (US); Gregory A. Daniels, Pacific Palisades, CA (US); Richard A. Berg, Los Altos, CA (US); Ronald A. Hitzeman, Pacifica, CA (US); George E. Chisholm, San Mateo, CA (US)

(73) Assignees: Cohesion Technologies, Inc., Palo Alto, CA (US); Genotypes, Inc., Pacifica, CA (US)

( * ) Notice: Subject to any disclaimer, the term of this patent is extended or adjusted under 35 U.S.C. 154(b) by 0 days.

(21) Appl. No.: 09/120,561

(22) Filed: Jul. 22, 1998

Related U.S. Application Data

(63) Continuation of application No. 08/546,047, filed on Oct. 20, 1995, now abandoned.

(51) Int. Cl.[7] .................................. C12P 21/06
(52) U.S. Cl. ................. 435/69.1; 435/69.1; 435/69.8; 435/233; 435/252.3; 435/254.1; 435/320.1; 530/350; 530/356; 536/23.1; 536/23.5; 536/23.2; 536/24.1
(58) Field of Search ............................. 435/69.1, 69.8, 435/233, 252.3, 254.1, 320.1; 530/350, 356; 536/23.1, 23.5, 24.1, 23.2

(56) References Cited

U.S. PATENT DOCUMENTS 5,405,757 A  * 4/1995 Prockop et al. ............ 435/69.1
5,593,859 A  * 1/1997 Prockop et al. ............ 435/69.1

FOREIGN PATENT DOCUMENTS

WO       WO 93/07889    *  4/1993

OTHER PUBLICATIONS

Robinson et al. (1994) Bio/Technology. 12:381–384.*
Hitzeman et al. (1990) Methods Enzymol. 185:421–441.*
Romanos et al. (1992) Yeast. 8:423–488.*
Gellissen et al. (1992) Antonie van Leeuwenhoek. 62:79–93.*

* cited by examiner

Primary Examiner—Karen Cochrane Carlson
Assistant Examiner—Hope A. Robinson
(74) Attorney, Agent, or Firm—Richard Aron Osman

(57) ABSTRACT

The invention discloses methods for effecting the production of recombinant mammalian procollagen in yeast, as well as compositions comprising yeast cells cap producing mammalian procollagen.

25 Claims, 26 Drawing Sheets

US 6,472,171 B1

EXPRESSION OF PROCOLLAGEN IN YEAST

CROSS REFERENCE TO RELATED APPLICATION

This application is a continuing application under 35 USC120 of U.S. Ser. No. 08/546,047 Oct. 20, 1995 now abandoned.

INTRODUCTION

1. Field of the Invention

The field of this invention is the production of recombinant procollagen in yeast.

2. Background

Collagen has provided a number of commercial applications, including use as a convenient substrate for cell culture, as well as in the manufacture of biocompatible materials (e.g. artificial skin) having a variety of therapeutic applications in humans. Commercially available collagens are primarily isolated from freshly killed farm animals such as cows and pigs in polymerized form or in soluble form derived by enzymatic or chemical treatment of polymerized collagen. However, polymerized collagens and soluble collagens derived from polymerized collagens are of limited usefulness due to the presence of natural crosslinks within the collagen. Furthermore, non-human collagen can provoke undesirable immune responses when administered to human subjects.

As one alternative, human collagen can be purified from human sources such as human placenta, as described in U.S. Pat. No. 5,002,071 (Research Development Foundation) and in copending U.S. application Ser. No. 07/921,810 (Collagen Corporation). In addition to source limitations and the risk of contamination by human pathogens such as Hepatitis viruses and HIV, the methods for recovering collagen from these sources bias the collagen type recovered. Furthermore, because the collagen is derived from naturally crosslinked tissues, the collagen recovered is not entirely homogeneous. Another approach is the expression of recombinant human collagen in the milk of transgenic animals, as described in copending U.S. applications Ser. Nos. 08/183,648 and 08/011,643 (Collagen Corporation). However, this approach subjects the recombinant collagen to any host deficiencies in translational processing.

The term collagen refers to a type of protein that encompasses a class of structurally-related polypeptides consisting of helical collagen chains and homo and heteromeric polymers thereof. Collagen chains often contain both long helical domains and non-helical extensions, or telopeptides. The helical domains comprise $—(GXY)_n—$ repeats, where X and/or Y are frequently proline or hydroxyproline.

Collagen chains are encoded by a number of related genes, See, Adams, S. L. Amer J Respir Cell and Mol Biol (1989) 1:161–168; Mayne and Brewton (1993) Current Opinion in Cell Biology 5:883–890; van der Rest and Bruckner (1993) Current Opinion in Structural Biology 3:430–436. Collagen-encoding transcripts are initially translated into procollagen chains which undergo a variety of post-translational events such as processing, secretion and assembly (e.g. disulfide exchange, lysyl residue hydroxylation, glycosylation, and crosslinking of the helical chains, see for example, Prockop et al. (1984) New England J Med 3111:376–386) to form mature collagen chain helices. In addition, procollagens contain N- and C-terminal propeptides that facilitate collagen formation, See, e.g. Lee et al. (1992) J Biol Chem 267, 24126–24133.

It is these unique properties of collagen, including the protein size and structure, the requisite postranslational processing, the secretory pathway, the nature of the collagen transcript and gene itself and its assembly into trimeric molecules, etc., that has severely restricted the ability of in vitro cellular expression systems to produce collagen or procollagen.

Relevant Literature

For reviews, see Nothwehr et al. (1994) J. Biol. Chem 269,10185–10188 re the sorting of membrane proteins in the yeast secretory pathway; Gellissen et al. (1992) van Leeuwenhoek 62, 79–93 re heterologous protein production in yeast; and, Hitzeman et al. (1990) Meth Enzymology 185, 421–441 re the use of signal sequences for secretion of heterologous proteins from yeast. Robinson et al. (1994) Biotechnology 12, 381–384 describes the use of protein disulfide isomerase overexpression to increase secretion of foreign proteins in yeast. Prockop et al. (1997) U.S Pat. No. 5,593,859 relates to synthesis of collagens in recombinant systems and Vuorela et al. (1997) EMBO J. 16, 6702–6712 reportedly expressed collagen proteins in *Pichia pastoris*.

SUMMARY OF THE INVENTION

The invention provides methods and compositions for making a mammalian procollagen in yeast. Generally, the subject methods involve (a) incubating a recombinant yeast cell comprising: (i) a stable genetic construct comprising in opposite orientations, first and second mammalian collagen genes operably linked to a first single divergent heterologous promoter; (ii) a prolyl hydroxylase gene; (iii) a protein disulfide isomerase gene, wherein the prolyl hydroxylase and protein disulfide isomerase genes are expressed to produce polypeptides that are associated into active proteins during the incubating step, in a medium under conditions wherein the collagen genes are expressed as procollagen chains and the chains secreted in the form of triple helical procollagen; and (b) recovering the triple helical procollagen. In various particular embodiments, the first single divergent heterologous promoter is a GAL1–10 promoter, the collagen genes reside on a plasmid or multiple integrants in the cell, the prolyl hydroxylase and protein disulfide isomerase genes are integrated into the genome of the yeast, the prolyl hydroxylase gene and protein disulfide isomerase genes are operably linked to a second single divergent heterologous promoter, the first and second single divergent heterologous promoters are the same, the protein disulfide isomerase gene comprises a signal sequence heterologous to the protein disulfide isomerase gene, the collagen and hydroxylase genes each comprise homologous secretion signal sequences, the medium comprises supplemental casein amino acids sufficient to promote the hydroxylation of the collagen under the conditions, the yeast cell is a *Saccharomyces cerevisiae* and the mammalian collagen genes are human collagen genes. The subject compositions include recombinant yeast cells useful for making a mammalian procollagen. Such cells generally comprise: (i) a stable genetic construct comprising in opposite orientations, first and second mammalian collagen genes operably linked to a first single divergent heterologous promoter; (ii) a prolyl hydroxylase gene; and (iii) a protein disulfide isomerase gene.

DETAILED DESCRIPTION OF PARTICULAR EMBODIMENTS OF THE INVENTION

Figure 1:
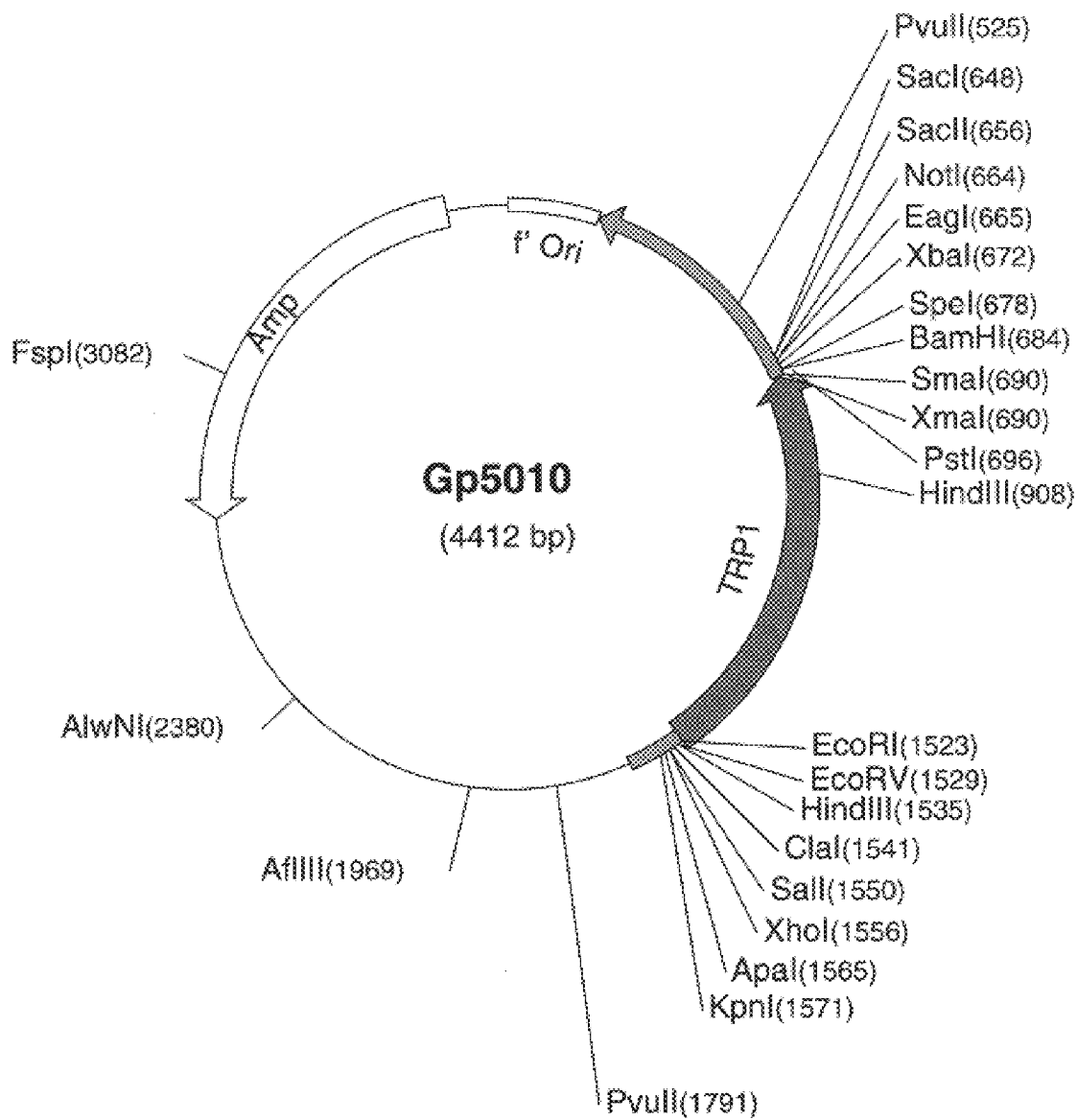
FIG. 1 illustrates the structure of plasmid Gp5010.

The invention provides a breakthrough in the ability to produce recombinant mammalian collagen in cultured yeast cells. In particular, the subject methods and compositions are used to produce commercially useful human collagen at commercially-feasible levels with low production costs.

The general methods involve incubating a recombinant yeast cell comprising a stable genetic construct, preferably maintained on a stable episomal plasmid in said yeast cell to maximize copy number and expression yield. The construct comprises mammalian collagen genes comprising signal sequences and operably-linked promoters heterologous or homologous to the collagen genes. The yeast cell is incubated in a medium under conditions wherein the collagen gene is expressed as a procollagen chain and secreted through the plasma membrane and, in a more particular embodiment, the cell wall of the yeast into the medium in the form of a triple helix procollagen. Finally, the expressed triple helix procollagen is recovered from the cells, periplasm and/or medium, e.g. by glass bead extraction. The collagen genes, signal sequences, promoters, yeast and incubation conditions are selected to maximize procollagen secretion, such that a detectable amount of, preferably most of, and more preferably substantially all of the procollagen chain expressed by the yeast cell is secreted through the plasma membrane and, in a more particular embodiment, the cell wall of the yeast.

The collagen gene used is selected from the closely related collagen gene family including α1-2(I), α1(II), α1(III), α1-6(IV), α1-3(V), α1-3(VI) α1(VII), α1(XIII), α1-3(IX), α1(X), α1-3(XI) and α1(XII). The basic structure, amino acid composition and codon usage of these genes are very similar and generally permit ready substitution of one collagen gene for another in the subject methods. See, e.g. Adams, S. L. Amer J Respir Cell and Mol Biol (1989) 1:161–168; Mayne and Brewton (1993) Current Opinion in Cell Biology 5:883–890; van der Rest and Bruckner (1993) Current Opinion in Structural Biology 3:430–436.

To produce heterologous collagens comprising different collagen chains (e.g. type I collagen comprises a heterotrimer of two α1(I) chains and a single α2(I) chain), the methods provide for the cointroduction of all requisite collagen genes into the host yeast cell for simultaneous expression. Association of the various collagen chains into multi-chain units is controlled at least partially by the relative supply of each chain. In some cases it is necessary to further bias the chain ratios to effect desired heterotrimers; for example, we find that heterotrimer with two α1(I) chains and one α2(I) chain form preferentially to three α1(I) homotrimers when both α1 and α2 are produced together in yeast cells.

The collagen structural gene requires a signal sequence capable of directing the nascent collagen chains through a secretory pathway to be posttranslationally processed and to effect efficient secretion of the collagen from the yeast into the periplasmic space. In the disclosed expression system, most, and preferably essentially all, of the secreted procollagen is secreted into the periplasmic space and, in a more particular embodiment, much, preferably most, and more preferably, essentially all of the secreted procollagen is secreted through the yeast cell wall as well. In particular, we identified the yeast α factor prepro sequence, the human HSA prepro sequence and the native α(I) collagen prepro sequence as providing signal sequences capable of effecting the secretion of substantially all of the expressed procollagen. Additional suitable signal sequences are identified empirically as described in Example 3 below.

The collagen gene and signal sequence are operably linked to a promoter heterologous to the collagen. A wide variety of constitutive and inducible promoters can be used. In particular, we found the following heterologous promoters well-suited to the transcriptional regulation necessary to practice the subject methods (See, Romano, et al. (1992) *Yeast* 8, 423–488):

| GAL1–10** | CHELATIN | PGK | GAP | TPI | GAP/GAL/GAP*** |
|---|---|---|---|---|---|
| ADH2 | PHO5 | Mfα1&2 | PGK/α2* | TPI/α2* | MAL61/MAL62*** |
| PGK/GAL* | GAP/ADH2* | GAP/PHO5* | CYC1/GRE* | PGK/ARE* | GAP/GAL* |

*denotes a hybrid promoter;
**denotes a divergent promoter.

In a particular embodiment, the collagen construct comprises in opposite orientations first and second collagen genes operably linked to a single divergent heterologous (to the collagen gene) promoter. A variety of divergent, or dual, promoters may be used to provide for the coordinate expression of the two collagen genes (Schneider K, Beck C F (1986) Gene 42(1):37–48), e.g. GAL1–10 promoters (Camilloni G, et al. (1986) EMBO J 5(4): 763–771 and West R W Jr, et al. (1987) Genes Dev 1(10): 1118–1131), MAL6T-MAL6S promoters (Bell P J, et al. (1995) Curr Genet 28(5), 441–446), etc. Preferred divergent promoters provide simultaneous and approximately equivalent transcriptional activation in both directions, as GAL1–10.

The host yeast cell provides a means or marker to select for recombinant cells which have been stably transformed with the collagen construct. Essentially any convenient means or marker which provides a convenient means for positive or negative selection may be used. Generally, the means or marker is a gene introduced into the host cell which confers on the cell a selective growth or survival advantage in one or more environments. Some examples of suitable selectable markers include an invertase gene, LEU2 (d) or TRP1. Alternatively, the expressed procollagen itself can provide selective or screening means. For example, automated fluorescent activated cell sorting (FACS) is conveniently used to segregate procollagen-expressing cells labeled with fluorescein-labeled anti-collagen antibody. In addition, procollagen expressing cells can be selected by secondary phenotype alterations caused by procollagen expression, such as an increased tendency for the cells to aggregate.

Any convenient yeast host cell may be used in the subject methods; for examples, well-established transfection and expression systems are available for *Saccharomyces cerevisiae* and *S. pombi*. In a preferred embodiment, *Saccharomyces cerevisiae* is used. In addition to the collagen construct and selectable marker, the recombinant yeast cells may also comprise additional genetic elements to improve yield and/or provide additional post-translational processing. For example, in one embodiment, the yeast cells cell further comprise a prolyl hydroxylase gene and a protein disulfide isomerase gene. In a particular embodiment, the prolyl hydroxylase and protein disulfide isomerase gene are integrated into the host cell chromatin, preferably operably linked to a divergent promoter, preferably a divergent promoter that is coordinately activated and inhibited with the divergent promoter used with and, preferably consists essentially of the same nucleotide sequence used for the plasmid-expressed collagen genes, more preferably the same divergent promoter used for the plasmid-born collagen genes, i.e. they both use a GAL1–10 promoter, a MAL61–MAL62 promoter, etc. In another particular embodiment, the protein disulfide isomerase gene comprises a heterologous (to the isomerase gene) signal sequence, preferably a yeast signal sequence, such as preinvertase or α-mating factor signal sequence. The yeast may also express an exogenous site-specific proteolytic agents capable of specifically cleaving the procollagen at the propeptide recognition site to provide mature collagen.

In one specific embodiment of the invention, the host yeast cells have one or more mutations that cause the cell wall of the yeast cell to exhibit increased permeability to large molecular weight proteins such as procollagen. Typically these mutations are in the synthetic pathway of the major wall proteins, such as chitin synthetase and glucan synthetase, e.g. mnn9, och1, och2, alg1, alg2, etc. In this embodiment, we find that procollagen expression can enhance the stability of the genetically defective walls, providing another means for selection. For example, the cells can be grown under stress-conditions which provide procollagen-expressing cells preferential growth or survival. Suitable stress-conditions for such selection include the presence of denaturing reagents such as detergents (e.g. 0.01% SDS), urea, etc.

A specific embodiment of the invention is defined by low temperature incubation conditions, which we found to be useful for efficient production of heterotrimer or homotrimer procollagen in yeast without the hydroxylation system. In particular, efficient expression of trihelical procollagen was found to occur at incubations performed at between about 15° C. and about 25° C., preferably at about 20° C. (with the hydroxylation system, the preferred growth temperature was about 30° C.). In addition, to facilitating efficient expression at these reduced temperatures where stable nonhydroxylated trimer formation otherwise predominates, the conventional minimal media used in expression should be provided supplemental amino acids. In fact, irrespective of incubation temperature, proper expression, particularly collagen hydroxylation, is promoted by the presences of supplemental casein-derived amino acids, e.g. 2.5–5 mg total casein-derived amino acids (CAA) per ml incubation medium. This effect has been duplicated with an equivalent concentration of one or more amino acids such as Arg, Lys and Glu, which are degraded in the cell to α-ketoglutarate, a substrate for hydroxylation.

Procollagen and/or collagen is purified from the medium or cells by methods known in the art; see, e.g. Miller and Rhodes (1982) Methods in Enzymology 82:33–64; Sage and Bernstein (1982) Methods in Enzymology 82:96–127. Resultant collagen compositions may be sterilized, e.g. by passage through 0.2 μm filters, (Millipore). Sterility may be confirmed by, for example, culturing aliquots on nutrient agar for at least 72 hrs at 30 and 37° C. For therapeutic uses, it is desirable to ensure the non-toxicity, biocompatibility and non-immunogenicity of the resultant recombinant collagen compositions. For example, non-immunogenicity in humans is confirmed by dermal sensitivity testing.

The invention provides a wide variety of applications of the subject recombinant procollagens and collagens in tissue and cell culture and therapy. For example, the subject procollagens and collagens are used to promote adhesion and growth of cells on a wide variety of solid substrates in various forms such as slides, filaments, sheets, plates, flasks, bottles, fibers, etc., and compositions such as plastics, glass, metals, saccharide-based polymers, etc. The collagens provide a wide range of therapeutic applications such as use in biodegradable sutures, synthetic dermal skin, biodegradable hemostatic sponges, tissue augmentation (including modifying localized soft tissue appearance), etc. Tissue augmentation using collagen compositions has been thoroughly studied, documented, and implemented in wide-spread clinical settings; see, e.g. DeLustro et al. (1986) J Biomed Mater Res, 20, 109–120; Elson M L (1989) J Dermatol Surg Oncol, 15, 301–303; Elson M L (1992) Am J Cosmetic Surg 9, 267–271; Klein et al. (1985) J Dermatol Surg Oncol, 11, 337–339; Klein et al. (1989) Geriatric Dermatology: Clinical Diagnosis and Practical Therapy, chapter 8, pp 47–49, Igaku-Shoin (publ) New York; Kligman A M (1988) J Dermatol Surg Oncol 14 (suppl I), 35–38; Kligman et al. (1986) J Dermatol Surg Oncol, 12, 351–357; Kligman et al. (1988) J Dermatol Surg Oncol, 14 (suppl I), 10–12; Knapp et al. (1977) Plas Reconstr Surg, 60, 398–405; Knapp et al. (1977) J Surg Res, 23, 96–105; Vamavides et al. (1987) Br J Dermatol 116, 199–206; etc.

The following examples are offered by way of illustration and not by way of limitation.

EXAMPLES

Example 1

Making of Precursor Plasmid (Gp5000) for the Construction of Gp5020 and Gp5012 which Contain the GAL1–10 Dual Promoter and Chelatin Promoter Respectively A construct containing yeast (2 micron origin, TRP1 gene) and bacterial (pBR322 functions) sequences known as YEp9T [C. Chen, H. Oppermann, and R. Hitzeman, Nuc. Acids Res. (1984) 12:8951–8970] was modified with a synthetic polylinker between a NdeI site in 2 micron DNA and a second NdeI site near the origin of pBR322. The polylinker sequence used was as follows: (NdeI) PvuII ApaI BglII ClaI NheI XhoI EcoRI BamHI AflII NotI (NdeI) (shown in Table 1). Sequencing verified that the DNA sequence in one clone (Gp5000) contained one copy of these restriction sites. Both NdeI sites were mutated so they no longer cut. All restriction sites are adjacent. This plasmid is not shown but can easily be visualized by examination of the polylinkers on both sides of the promoters in Gp5020 (GAL1–10 promoter) and Gp5012 (chelatin promoter).

synthetic BamHI site added to −6 of GAL1 has long been used as a non fusion end of a GAL1 promoter; while the normal EcoRI site at the other end produces a partial fusion protein from GAL10-heterologous gene fusions in one reading frame. We therefore used a PCR primer at the other end to place an EcoRI site onto −1 of the GAL10 gene as GAATTC. An EcoRI/BamHI (SEQ ID NO:3) fragment of 687 bp was removed from the pUC cloning vector and placed in EcoRI/BamHI sites of Gp5000 to make Gp5020. Both sides of this dual promoter are inducible with galactose and repressible by glucose. Now it can be used to produce two different heterologous gene products containing their own ATG translation starts.

TABLE 1

```
            Sau3A  I
         Sau96  I                                    Mse  I
         Hae  III                                    Afl  II
         Sau96  I                                    Bsl  I
         Nla   IV                                    Sau3A  I
         Bsp1286  I                                  Mbo  I
         Bsp120  I          Taq  I       Xho  I      Dpn  II       BstU  I
         Ban  II            Cla  I       PaeR7  I    Dpn  I        Fnu4H  I
         Apa  I      Mbo  I              BsoB  I     Nla  IV       Hae III
         Nla  IV     Dpn  II    Bfa  I       EcoR  I    BsiY  I    Eag  I
         EcoO109     I    BspD  I       Ava  I        BstY  I      Eae  I
  Alu  I             Dpn  I    Nhe  I    Taq  I      BamH  I       BsiE  I
  Pvu  II            BstY  I   Cac8  I   Mn1  I      Alw  I        Not  I
(NdeI)  MapA1  I    Bgl II    SfaN  I   Mn1  I  Apo I  Alw  I     Fnu4H  I   (NdeI)
        ||    |||   ||  |||   || |  ||   |||  |•  |    ||• |||    ||||  |   •
    CATATCAGCTGGGGCCCAGATCTATCGATGCTAGCCTCGAGGAATTCGGATCCTTAAGGCGGCCGCGATATG  72  (SEQ ID NO: 10)
    GTATAGTCGACCCCGGGTCTAGATAGCTACGATCGGAGCTCCTTAAGCCTAGGAATTCCGCCGGCGCTATAC
        ||   •|||   ||•  || |  ||   |||  |•  |     ||• |||     ||||  |    •
        6          18       27    35      42      49           59
        6          18          30       39       48           59
          7        19          30       37       48           60
```

Two yeast promoter fragments were isolated from highly expressed yeast genes using the polymerase chain reaction (PCR) [K. Mullis and F. Faloona, Methods in Enzymology (1987) 155:335] with genomic DNA from yeast strain, S1799D (a trp5 his4 ade6 gal2) [J. Moss, Biophys. Res. Comm. (1964) 18:850] using an EcoRI site on one end and a BamHI site on the other end. DNA sequences used for primers were from these sources: chelatin [T. R. Butt, et al., Proc. Natl. Acad. Sci. USA (1984) 81:3332 and M. Karin et al, Proc. Natl. Acad. Sci. USA (1984) 81: 337–341] and GAL1–10 promoters [M. Johnston and R. Davis, Molecular and Cellular Biol. (1984) 4: 1440–1448].

An EcoRI site was placed on the 5' sequence end of the chelatin gene next to the −460 bp (upstream of chelatin ATG) which also contains a natural BamHI site that is retained after PCR (SEQ ID NO:1). On the other end next to the ATG is deleted 10 bp (up to −10) and replaced with ATCTAGAATTC (SEQ ID NO:2, XbaI site and EcoRI site). The BamHI/EcoRI fragment generated by this PCR and isolated in a pUC vector was placed in Gp5000 after cutting both with BamHI and EcoRI to make Gp5012 containing a 454 bp fragment. This promoter is inducible in shake flasks using 0.2 mM CuSO4.

An EcoRI site was placed at the beginning and end of the GAL1–10 promoter in such a way as to make both the GAL10 end and GAL1 end usable as a dual divergent promoter for non fusions of heterologous gene proteins. The Example 2
Native Procollagen Yeast Expression Vector The human α1(I) procollagen cDNA is described in A. Stacy, R. Mulligan, R. Jaenisch (1987) J. Virol. 61, 2549–2554. The human α1(I) procollagen cDNA was cloned into Bluescript II between the EcoRI and SspI sites (Stratagene Cloning Systems, La Jolla, Calif.), generating pDT2025, and from this vector recloned either between the SalI and SnaBI sites of pSV-SPORT1 (Gibco-BRL, Gaithersburg, Md.), generating construct pDT2067, or between the HindIII and EcoRV sites of pcDNA3 (Invitrogen Corporation, San Diego, Calif.), yielding construct pDT2068. The 4550 bp XbaI fragment from pDT2068 was cloned into yeast expression vectors Gp5012 and Gp5020 using the NheI site in the polylinkers. Plasmids Gp5105 and Gp5106 resulted from this attempt. It should be noted that the structure of the 3' end of this construct is different from that in Gp5101 and Gp5102 (see description in Example 3). A number of extra sites, including a second NotI site have been introduced by the inclusion of a small portion of the polylinker from the pDT2068 from which the XbaI fragment was isolated. To work on yield improvement, it would be desirable to only have the one unique NotI site located 5' to the yeast promoter at coordinate 5057 bp in Gp5105 map. To accomplish this we isolated the NotI–KpnI fragments from Gp5105 (620 bp) and Gp5106 (853 bp) containing the yeast promoter/collagen 5' end junction and cloned them into NotI–KpnI cut Gp5101 to create Gp5111 and Gp5112. These plasmids now have the native collagen secretion signal with the same 3' junction structure as the other expression constructs described in Example 3. They also now have only the one NotI site near the promoter element. All four of the native secretion signal constructions have been transformed into the following yeast strains:

| | |
|---|---|
| GY5196 | MATa leu2-Δ1 trp1-Δ63 ura3-52 his3-Δ200 GAL |
| GY5198 | MATa trp1-Δ63 ura3-52 GAL |

GY5196 and GY5198 were obtained from a genetic cross of X2180-1B (Yeast Genetic Stock Center Catalog, U. C. Berkeley, 7th Addition, 1991) and YPH499 (Sikorski and Hieler (1989) *Genetics* 112, 19–27). Selection for Trp$^+$ complementation (*Current Protocols in Molecular Biology*, (Kaaren Janssen, Ed.) Chapter 13, John Wiley & Sons, USA) has yielded hundreds of transformants for each plasmid.

Example 3
Procollagen Yeast Expression Vector with Altered Secretion Signal

Altering the 5' end of the α1(I) collagen coding region to remove the native secretion signal would allow us to add various heterologous and homologous secretion signals which previously have worked well in yeast. Oligonucleotide primers were used in the PCR™ reaction (H. A. Erlich, D. Gelfand, J. J. Sninsky (1991) *Science* 252, 1643–1651), and the product was cloned into vector pUC118 for DNA sequencing. We cloned the PCR product from the above plasmid into our expression vectors containing a synthetic prepro-HSA secretion signal (R. Hitzeman, et al. (1990) *Meth. Enzymol* 185, 421–440) using the BglII and SalI sites generating plasmids Gp5099 and Gp5100 respectively. We then added the rest of the α1(I) procollagen coding region by ligating the 4389 bp KpnI–SspI fragment from pDT2025 to KpnI–PvuII digested vectors Gp5099 and Gp5100 to generate plasmids Gp5101 and Gp5102 respectively.

We have also constructed plasmids that contain the yeast α factor prepro sequence joined to the α1(I) procollagen coding region. The first step was to clone the 525 bp BglII–SalI α(I) collagen PCR fragment into BglII–SalI cut vectors Gp5096 and Gp5097 to generate plasmids Gp5107 and Gp5108. Vectors Gp5096 and Gp5097 contain the yeast chromosomal α factor prepro sequence isolated by PCR from yeast strain 20B-12 (Jones (1977) *Genetics* 85, 23–33) using DNA sequence (Kurjan and Herskowitz (1982) *Cell* 30, 933–943) in our expression vector with either the chelatin (Etcheverry (1990) *Meth. Enzymol.* 185, 319–327) or GAL1–10 (Johnson, et al. (1987) *Cell* 50, 143–146) promoter elements, respectively. The next step was to clone the KpnI–NotI fragments from plasmids Gp5107 and Gp5108 (802 bp and 1035 bp respectively) into KpnI–NotI cut Gp5101 vector to generate expression plasmids Gp5113 and Gp5114. Both α factor prepro procollagen α1(I) expression plasmids have been transformed into yeast for analysis.

Example 4
Collagen Expression Studies

Analysis of yeast extracts by SDS indicated there are no major yeast proteins that co-migrate in the region where we would expect α1(I) procollagen to be on either 5% or 8% SDS:PAGE gels (U. K. Laemmli (1970) *Nature* 227, 680–685). A 'collagenase' activity was identified in the periplasmic preparations of yeast extracts. The 'collagenase' activity appears to be derived from the enzyme preparation (Zymolyase T100, ICN Biochemicals) used to lyse the yeast cell wall and release the periplasmic proteins. We found that this activity seemed to be processing the procollagen to collagen and could be inhibited by PMSF indicating the involvement of a serine protease.

Yeast transformants were grown for 72 hr at 10°, 20°, 25°, or 30° C. in selective medium in the presence or the absence of inducer (0.2 mM copper sulfate for the chelatin promoter and 2% galactose for the GAL1–10 promoter). Twenty O.D. unit pellets (equivalent of 20 ml of cells at O.D.$_{600}$=1.0) were collected and resuspended in 100 ml of SDS sample buffer or phosphate-buffered saline plus 5 mMEDTA and 1 mM PMSF (PBS). Acid washed glass beads (Sigma, St. Louis, Mo.) were added and the sample vortexed at room temperature for 6–15 min. SDS sample buffer was added to samples resuspended in PBS. The samples were incubated at 95° C. for 5 min and the debris was collected by centrifugation. Clarified supernatants were loaded onto 6% SDS:PAGE gels. The gels were western blotted (H. Towbin, T. Staehelin, and J. Gordon (1979) *Proc. Nat. Acad. Sci.* 76, 4350–4354) onto PVDF membranes (Millipore Corp., Bedford, Mass.), probed using an antibody against the amino-propeptide region of human α1(I) procollagen (LF-39, L. W. Fisher, W. Lindner, M. F. Young, and John. D. Termine (1989) *Connective Tissue Res.* 21, 43–50) and a horseradish peroxidase-inked secondary detection antibody (Kirkegaard and Perry, Gaithersburg, Md.), followed by development using the ECL™ Detection Kit (Amersham Life Science, Inc., Arlington Heights, Ill.). Results of the analysis showed the presence of antibody-reactive protein migrating in the expected location for α1(I) procollagen. To further confirm that yeast transformed with the human α1(I) procollagen cDNA was directing the synthesis of procollagen protein, yeast extract was treated with bacterial collagenase (Bacterial Collagenase Form III, Advance Biofractures Corp., Lynbrook, N.Y.), which digests the triple helical region of procollagen. The results demonstrate the sensitivity of the antibody-reactive band to this enzyme.

Example 5
Quantitation of α1(I) Procollagen Synthesized in Yeast

Human α1(I) procollagen was isolated from SVWI-38 cells (M. I. Parker, A. A. Smith, K. Mundell, M. Collins, S. Boast, and F. Ramirez (1992) *Nuc. Acids Res.* 20, 5825–5830) and used as a standard to quantify human α1(I) procollagen produced by yeast. Both the SVWI-38 derived procollagen and yeast extract were diluted, run on 6% SDS:PAGE, and western blotted using LF-39 antibody. A comparison of relative signal strength between the standard and the procollagen in the yeast extract was used to estimate the amount procollagen in the yeast extract. The total protein concentration of the yeast extract was determined using the BCA Protein Kit (Pierce, Rockford, Ill.). Based on the protein assay, the amount of α1(I) procollagen produced was approximately 0.3% of the total protein in the yeast extract. Visible bands on silver stains of SDS gels suggest that levels of the collagen may be much higher. Since the antibody recognizes the amino-terminal portion of procollagen, processed forms of procollagen are not detected by the western blotting method.

The relative intensities of anti-collagen antibody-reactive material in western blots were compared between yeast transfections using the two different promoters, the three different leader sequences linked to the human α1(I) procollagen cDNA, and the two yeast strains. Both yeast promoters produce procollagen. The level of procollagen produced using the three different secretion signals has the following relationship:

preproα factor-procollagen>preproHSA-procollagen>preprocollagen.

Example 6
Growth Characteristics of Yeast Producing Human Procollagen

Figure 24:
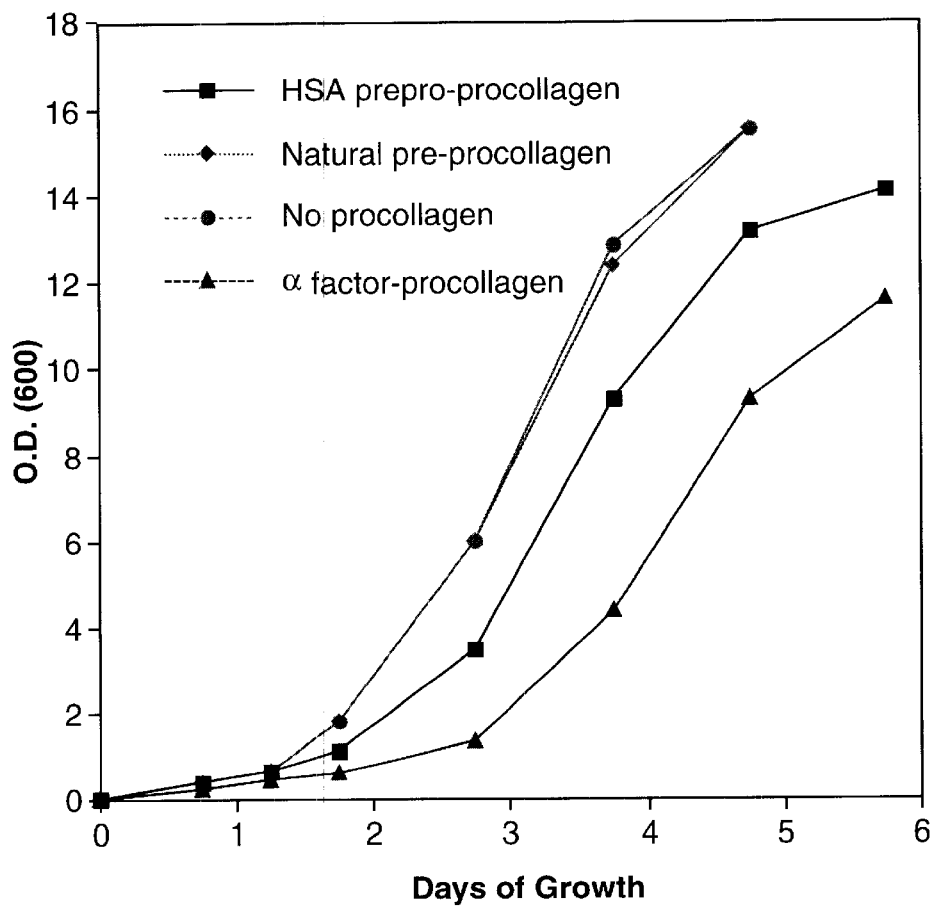
FIG. 24 illustrates the rate of increase in $O.D._{600}$ of transformed *S. cerevisiae* cultures grown at 20° C. for several days. Each transformed *S. cerevisiae* culture harbors a multicopy plasmid containing a different leader sequence linked to the human α1(I) procollagen gene. The control sample is a transformed *S. cerevisiae* culture which contains a multicopy plasmid without the human α1(I) procollagen gene.

FIG. 24 shows growth curves of yeast induced for procollagen production (medias are identical) at 20° C. where the only variables are +/- the procollagen gene expression and three different secretion signals on the same human procollagen protein. The native human procollagen signal results in no growth rate difference as compared to a nonprocollagen producing strain (same plasmid present but without the procollagen gene), while the other two secretory signals result in a significant decrease in growth rate (especially with the α factor prepro signal). The growth, although slowed, does eventually reach the same stationary phase. However, this does suggest a possible advantage of using the natural secretion signal (which along with the other two signals puts procollagen in the periplasm of the yeast cell as discussed in Example 7 below).

A visible yeast characteristic is noticed under the microscope in a direct relationship with this slow growth: yeast cell clumping (lack of efficient mother/daughter cell separation after mitosis). This characteristic often coincides with cell wall changes or defects. This clumping is extremely dramatic for yeast producing secreted procollagen using the a factor prepro sequence.

Example 7
Localization of the Human Procollagen Produced in Yeast

Yeast fractionation experiments were done according to R. Hitzeman et al. (1983) *Nuc. Acids Res.* 11, 2745–2763, and Current Protocols of Molecular Biology. Yeast containing the human α1(I) procollagen cDNA were fractionated into intracellular, periplasmic, and media fractions. Media was concentrated approximately 40-fold using CentriCell 20 centrifugation. Each fraction was electrophoresed on a 6% SDS:PAGE and western blotted. Most the procollagen was found in in the extracellular periplasmic (50–100%) and media fractions.

Example 8
Trimeric Formation of the Human Procollagen Produced in Yeast The triple helical region of the procollagen molecule, comprised of three polypeptide chains in the correct orientation, is resistant to endoproteases such as trypsin, chymotrypsin, and pepsin (P. Bruchner and D. J. Prockop (1981) *Anal. Biochem.* 110, 360–368). Mammalian α1(I) procollagen triple helical molecules are stable to>37° C. due to hydroxylation of proline residues within the triple helical region of the procollagen molecule (A. E. Geddis, D. J. Prockop (1993) *Matrix* 13, 399–405). To determine whether the human α1(I) procollagen polypeptides synthesized in yeast are associating into the correct triple helical structure, yeast extracts containing the preproHSA-procollagen were digested with pepsin (Worthington Biochemical Corp., Frehold, N.J.) at increasing temperatures. Using a 6% SDS:PAGE stained with the Silver Stain Plus Kit (Bio-Rad Laboratories, Hercules, Calif.), we showed that the triple helical region of the α1(I) procollagen protein is resistant to pepsin digestion at 20° and 23° C. At higher temperatures, the collagen band disappears, which suggests that the triple helix is dissociating and thereby susceptible to pepsin digestion. Yeast does not synthesize the enzyme necessary to hydroxylate procollagens. The melting temperature (Tm) of the triple helix of α1(I) procollagen synthesized by yeast is what would be expected for an unhydroxylated procollagen (R. A. Berg and D. J. Prockop (1973) *Biochem. Biophys. Res. Commun.* 52, 115–120).

An experiment to determine the Tm of SVWI-38-derived procollagen showed that the triple helix was stable to >38° C., with the hydroxylation system present during growth at 30° C. Our earlier results showed that yeast produced human procollagen can be secreted from the yeast cell and presented in the periplasm or media, and strain selection can be used to predetermine where (cell, perplasm, medium) most of the procollagen will be presented.

Example 9
Plasmid Copy Number Increase

Our expression vector system was constructed with a unique NotI site (located at coordinate 740 on the GpS5020 map) to facilitate the addition of the LEU2(d) allele or other elements that might benefit gene expression. We have also previously constructed a plasmid (Gp5091) that contains the LEU2(d) allele as a NotI fragment (1369 bp). We have inserted the LEU2(d) allele in the various α(I) procollagen expression plasmids.

Example 10
Determination of Procollen Concentration

To determine the concentration of recombinant procollagen produced in the yeast extracts, we used a sandwich immunoassay with a chemiluminescent detection system using human placental collagen as the standard. Affinity purified goat anti-human type I collagen obtained from Biodesign (Kennebunk, Me.) was used as both the detection and the capture antibody. The antibody in this assay is specific for heterotrimeric human type I procollagen and will not detect homotrimeric or denatured procollagen. The capture antibody was biotinylated allowing the antibody to be captured from solution with magnetic beads which had been conjugated to streptavidin. The detection antibody was conjugated to a ruthenium chelate complex which allows chemiluminescent detection. The standards and appropriate dilutions of the samples were incubated for two hours at room temperature with both capture and detection antibodies in polypropylene tubes. At the end of the two hour incubation, streptavidin-conjugated magnetic beads were added, the sample was incubated an additional 30 min, and then analyzed on an ORIGEN immunoassay analyzer from IGEN (Gaithersburg, Md.).

Figure 2:
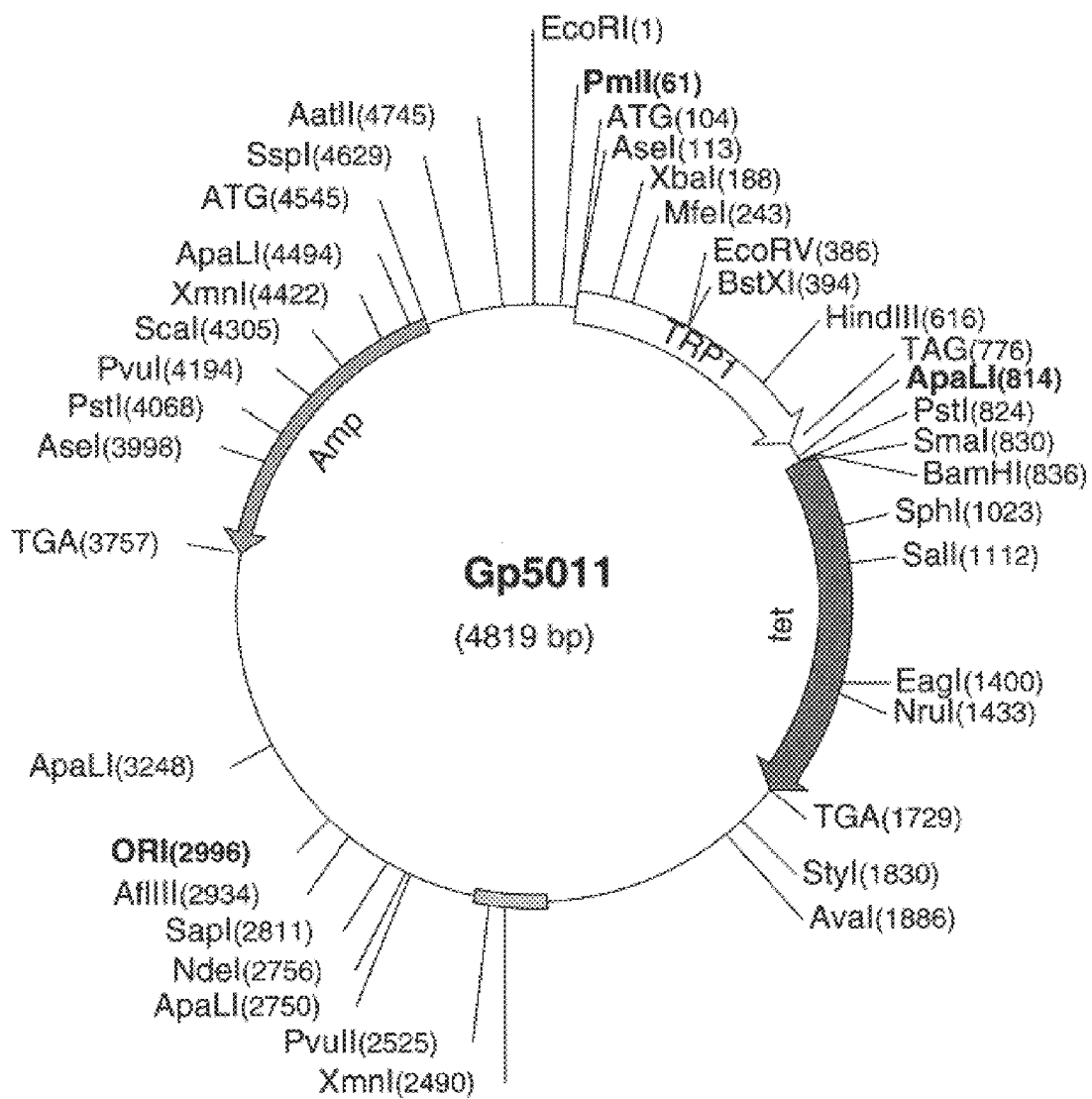
FIG. 2 illustrates the structure of plasmid Gp5011.
Figure 3:
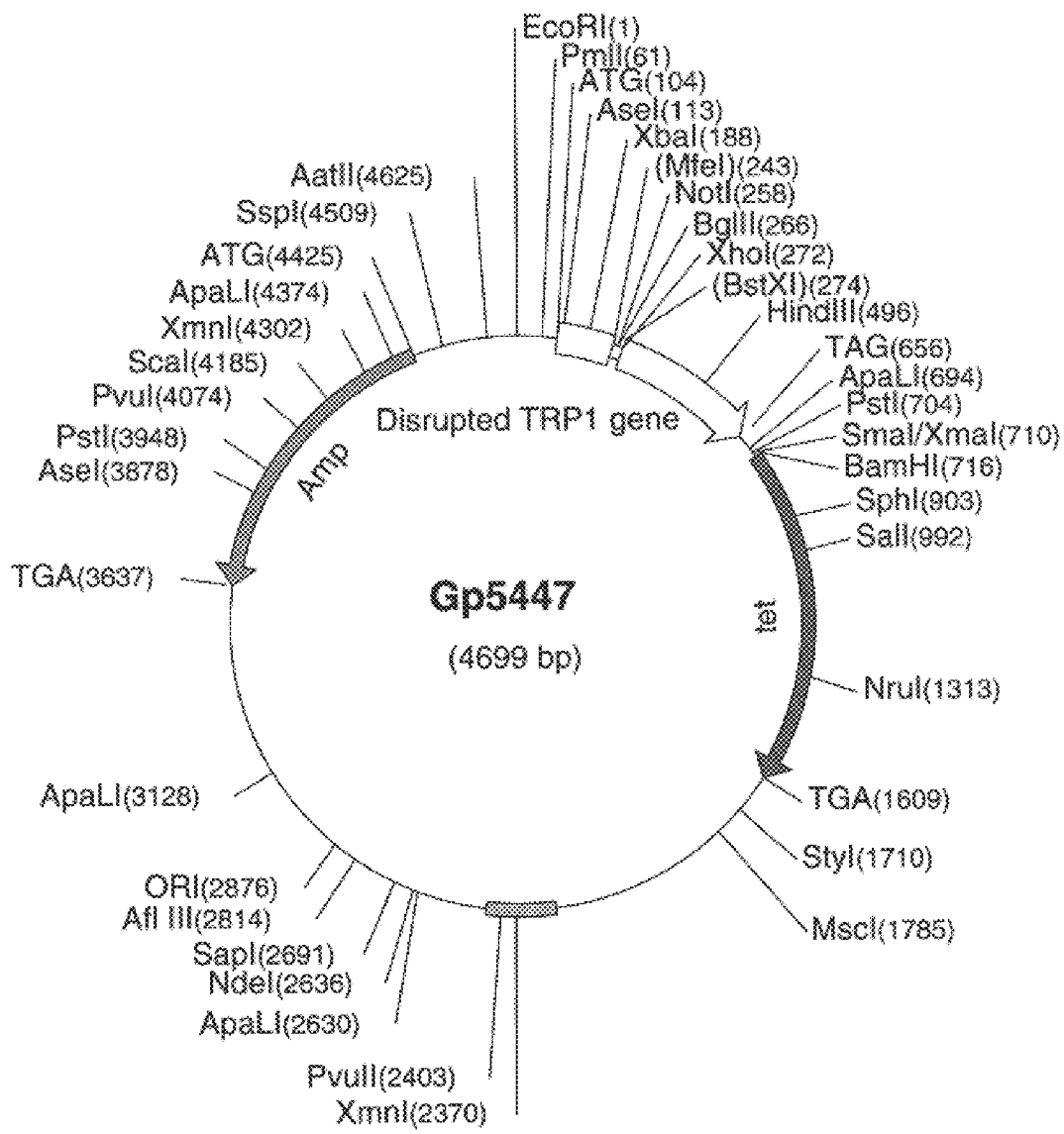
FIG. 3 illustrates the structure of plasmid Gp5447.

Example 11
Construction of Type I Procollagen Yeast Expression Vectors: TRP1 Integration Vector Construction The 1.45 kbp EcoRI fragment from YRp7 [G. Tschumper and J. Carbon, Gene (1980) 10, 157–166] containing the yeast TRP1 ARS1 chromosomal region, was cloned into EcoRI cut pBluescript II SK+. The resulting 632 bp PstI fragment was deleted (from the PstI site between TRP1 and ARS1 to the PstI site in the polylinker of the vector) to remove any ARS1 activity and to generate a BamHI site at the 3' end of the TRP1 gene (FIG. 1, plasmid Gp5010). The resulting 836 bp TRP1 fragment, EcoRI to BamHI, was cloned into EcoRI–BamHI cut pBR322 (FIG. 2, plasmid Gp5011). A linear fragment of the TRP1 gene, completely homologous with the chromosomal copy of TRP1 can be excised from this plasmid using PmlI and ApaLI (sites @61 bp and @814 bp respectively on plasmid Gp5011, FIG. 2). In order to add unique sites (XhoI, NotI, and BglII) into which other expression units could be added and integrated into the TRP1 locus of yeast and to ensure that no complete copy of TRP1 would remain after integration, a portion of the coding region, from the MfeI site @243 bp to the BstXI site @394 bp, was removed and replaced with oligonucleotides GN343 and GN344 to generate plasmid Gp5447 (Table 2 and FIG. 3).

TABLE 2

Oligonucleotides GN343 and GN344

```
       (MfeI)              NotI    BglII  XhoI
GN343 5'AATTGA TGA CTGA GCGGCCGC AGATCT CTCGAG CTGC 3' (SEQ ID NO:4)
GN344 3'    ACT ACT GACT CGCCGGCG TCTAGA GAGCTC      5'(SEQ ID NO:5)
             *   *    *      (* = STOP CODONS)
```

Figure 4:
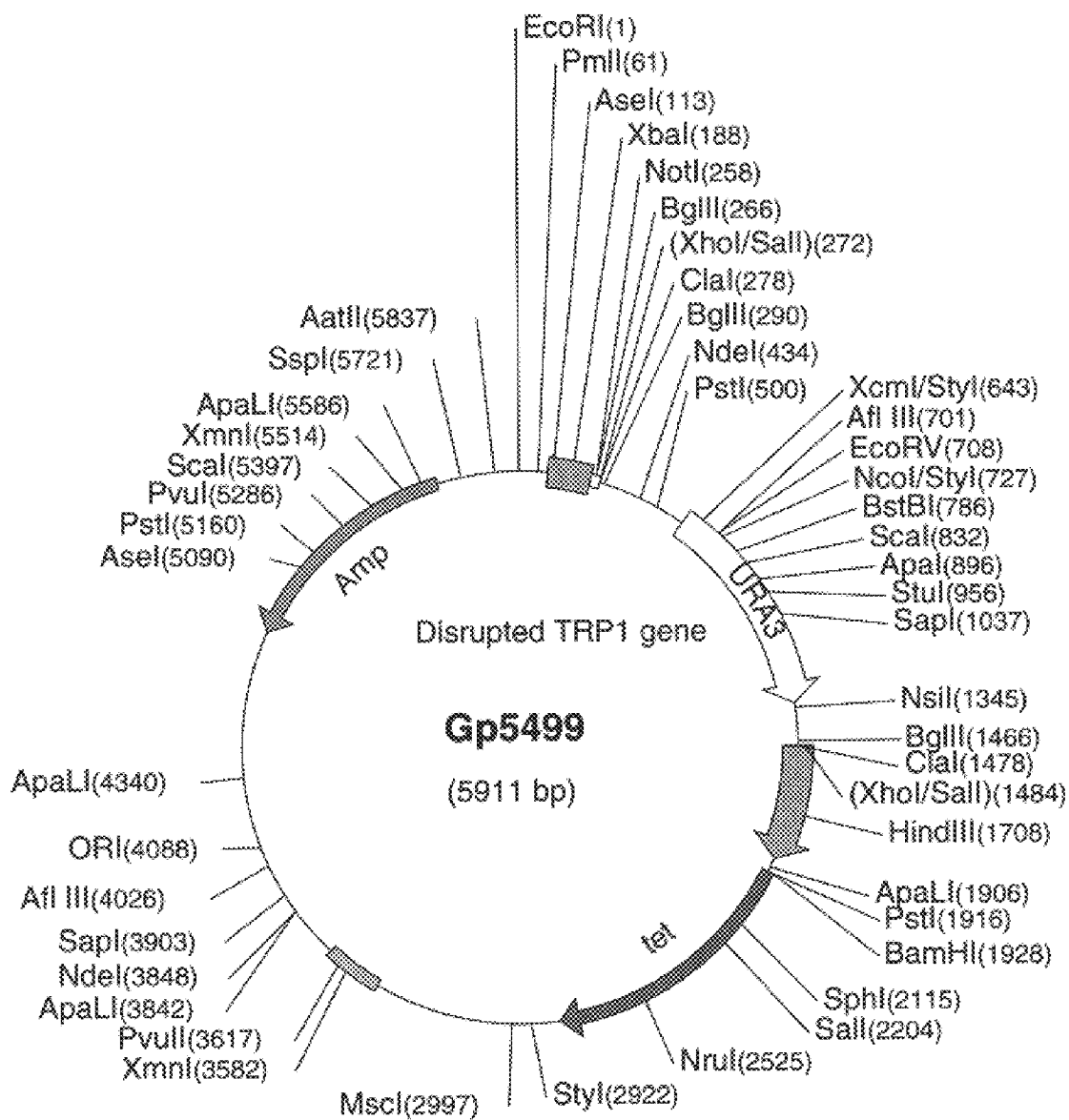
FIG. 4 illustrates the structure of plasmid Gp5499.

To complete the integration vector, a 1.2 kbp SalI fragment containing the yeast URA3 gene was cloned into the unique XhoI site to generate plasmid Gp5499 (FIG. 4). The URA3 gene, 1.16 kbp HindIII fragment [F. Fasiolo, J. Bonnet, and F. Lacroute, J. Biol. Chem. (1981) 56: 2324] converted to SalI ends with oligonucleotides, was added as a selectable marker to facilitate the identification of integration events.

Example 12

Construction of Type 1 Procollagen Yeast Expression Vectors: Hydroxylation System Integration Cassette Construction Plasmid Gp5341 (FIG. 5) depicts the starting structure for the construction of the final integration cassette. Several modifications have been made in constructing this plasmid. First; the polylinker normally found on our basic vector Gp5020 (described above) between the PvuII and EcoRI sites has been altered to give a second NotI site @17 bp, FIG. 5). This allows the final divergent expression cassette to be cloned into the unique NotI site of Gp5499 @258 bp, FIG. 4). Second; both the 5' and 3' ends of the chicken protein disulfide isomerase (cPDI) gene [J. A. Bassuk and R. A. Berg, Matrix: Collagen Relat. Res. (1989) 9: 244–248] were altered by PCR to allow the addition of the yeast alcohol dehydrogenase gene [J. L. Bennetzen and B. D. Hall, J. Biol. Chem. (1982) 257: 3018] transcription termination region (ADHt, 3330 bp HindIII fragment from sites 38 bp to 368 bp, FIG. 5) and the yeast pre-invertase secretion signal sequence from the SUC2 gene [C. N. Chang, et al., Mol. and Cell. Biol. (1986) 6: 1812–1819 and R. Taussig and M. Carlson, Nucleic Acids Res. (1983) 11: 1943–1954]. This synthetic signal was added to the 5' end (the region between 1888 bp and the EcoRI site @1935 bp, FIG. 5). After both altered ends of the PCR product were verified by DNA sequencing, the center portion (mostly unsequenced region of the PCR product) of the gene was replaced by a fragment from the original cDNA clone to ensure that no mutations were introduced by the PCR reaction. The 5' end was modified such that when the yeast pre-invertase secretion signal was added the signal peptidase cleavage site was maintained intact and would generate authentic mature cPDI protein. The yeast pre-invertase secretion signal sequence DNA was generated synthetically using 4 overlapping oligonucleotides and its structure was verified by DNA sequencing prior to fusion with the cPDI gene. Some codon changes occurred in this secretion signal for convenient addition of restriction sites (see FIG. 5, Table 3).

TABLE 3

Pre-invertase secretion signal sequence

```
EcoRI   XhoI    AflII                         HindIII
GAATTC CTCGAG CTTAAG ATG ATG CTT TTG CAA GCT TTC CTT TTC
CTTAAG GAGCTC GAATTC TAC TAC GAA AAC GTT CGA AAG GAA AAG
                      M   M   L   L   Q   A   F   L   F
NheI                                  (BssHII)
CTG CTA GCT GGT TTT GCA GCC AAA ATA AGC GCG GAG CCC CTG . . .
GAC GAT CGA CCA AAA CGT CGG TTT TAT TCG CGC CTC GGG GAC     (SEQ ID NO:6)
 L   L   A   G   F   A   A   K   I   S   A   E   P   L     (SEQ ID NO:7)
                                             mature cPDI
```

Figure 5:
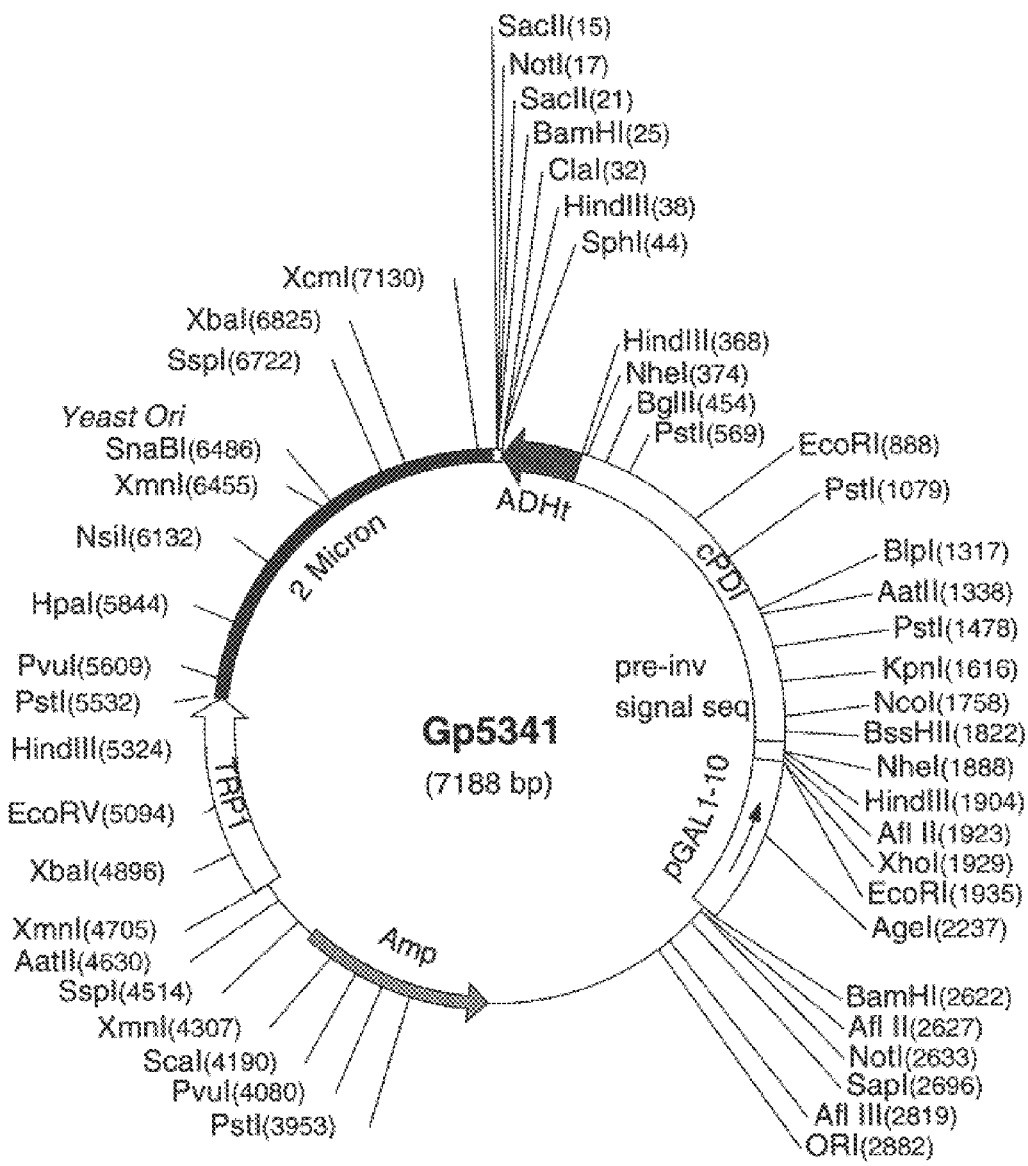
FIG. 5 illustrates the structure of plasmid Gp5341.

The 3' end of the cPDI gene was modified to allow the addition of the ADHt HindIII fragment just downstream of the cPDI translation stop codon to eliminate any non-yeast 3' untranslated regions in the mRNA. The yeast pre-invertase secretion signal—mature cPDI—ADHt expression unit was cloned between the EcoRI (@1935 bp) and the HindIII (@38 bp) sites to generate plasmid Gp5341 (FIG. 5). A heterologous (preinvertase) secretion signal sequence provided substantially enhanced hydroxylation as compared with the native cPDI signal.

Figure 6:
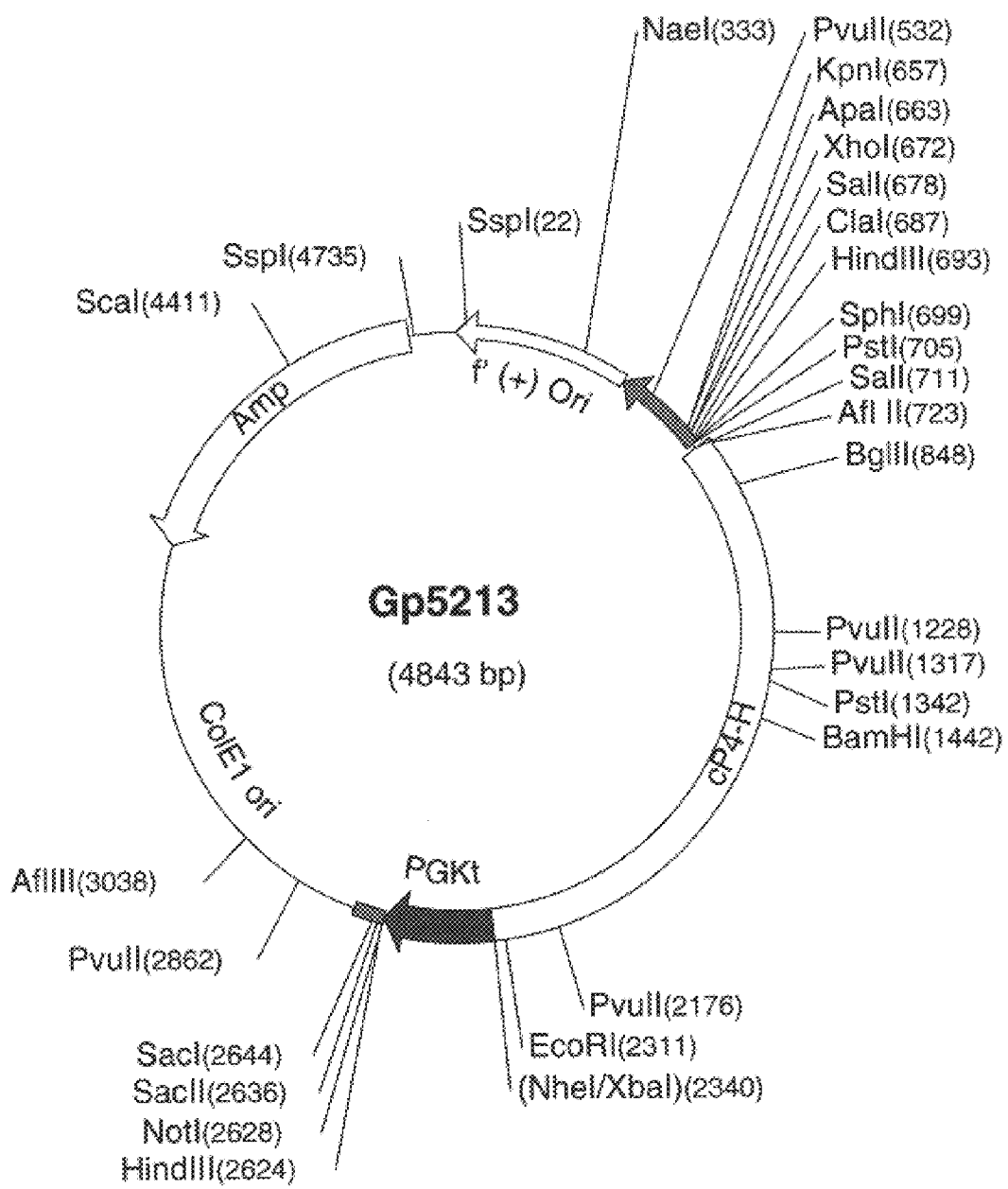
FIG. 6 illustrates the structure of plasmid Gp5213.

The plasmid Gp5213 (FIG. 6) depicts the structure of the yeast expression unit of the chicken prolyl 4-hydroxylase (cP4-H) subunit [J. A. Bassuk et al. Proc. Natl. Acad. Sci. USA (1989) 86: 7382–7386] of the hydroxylation complex. As with the cPDI gene, both the 5' and 3' ends of the cP4-H coding region were modified by PCR. After verification of the changes by DNA sequencing the center portion of the PCR product was replaced by a fragment from the original cP4-H cDNA clone to ensure that no changes were introduced into the coding region by the PCR reaction. An Afl II site was introduced at the 5' end just upstream of the cP4-H start (ATG) codon. For this construction the native secretion signal was left intact and not altered. A unique NheI site was introduced at the 3' end just downstream of the cP4-H translation stop codon to allow the addition of the yeast phosphoglycerate kinase gene [R. A. Hitzeman et al., Nucleic Acids Res. (1982) 10: 7791–7808] transcription termination region fragment (PGKt, XbaI site @2340 bp to the NotI site @2628 bp, FIG. 6).

Figure 7:
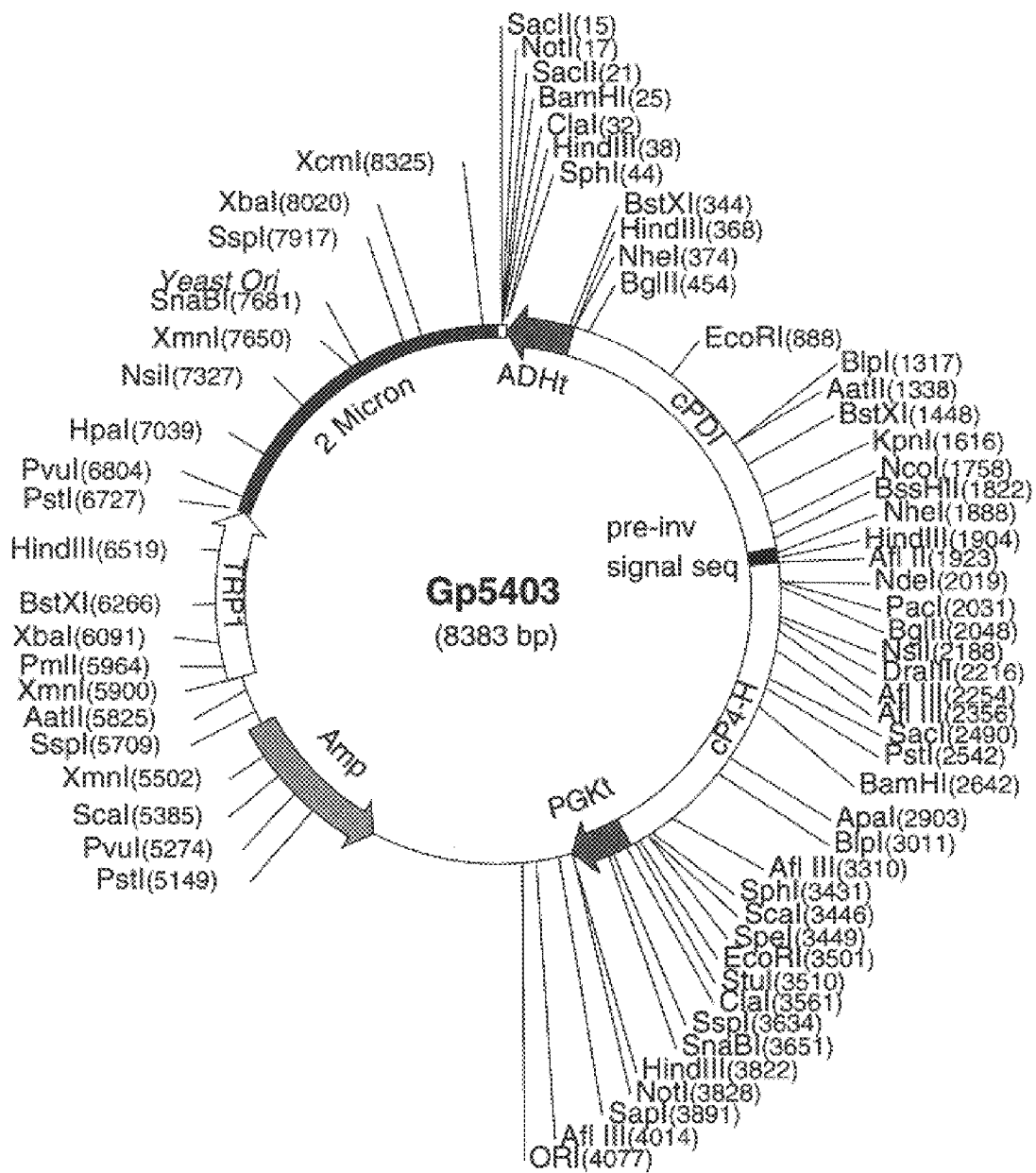
FIG. 7 illustrates the structure of plasmid Gp5403.
Figure 8:
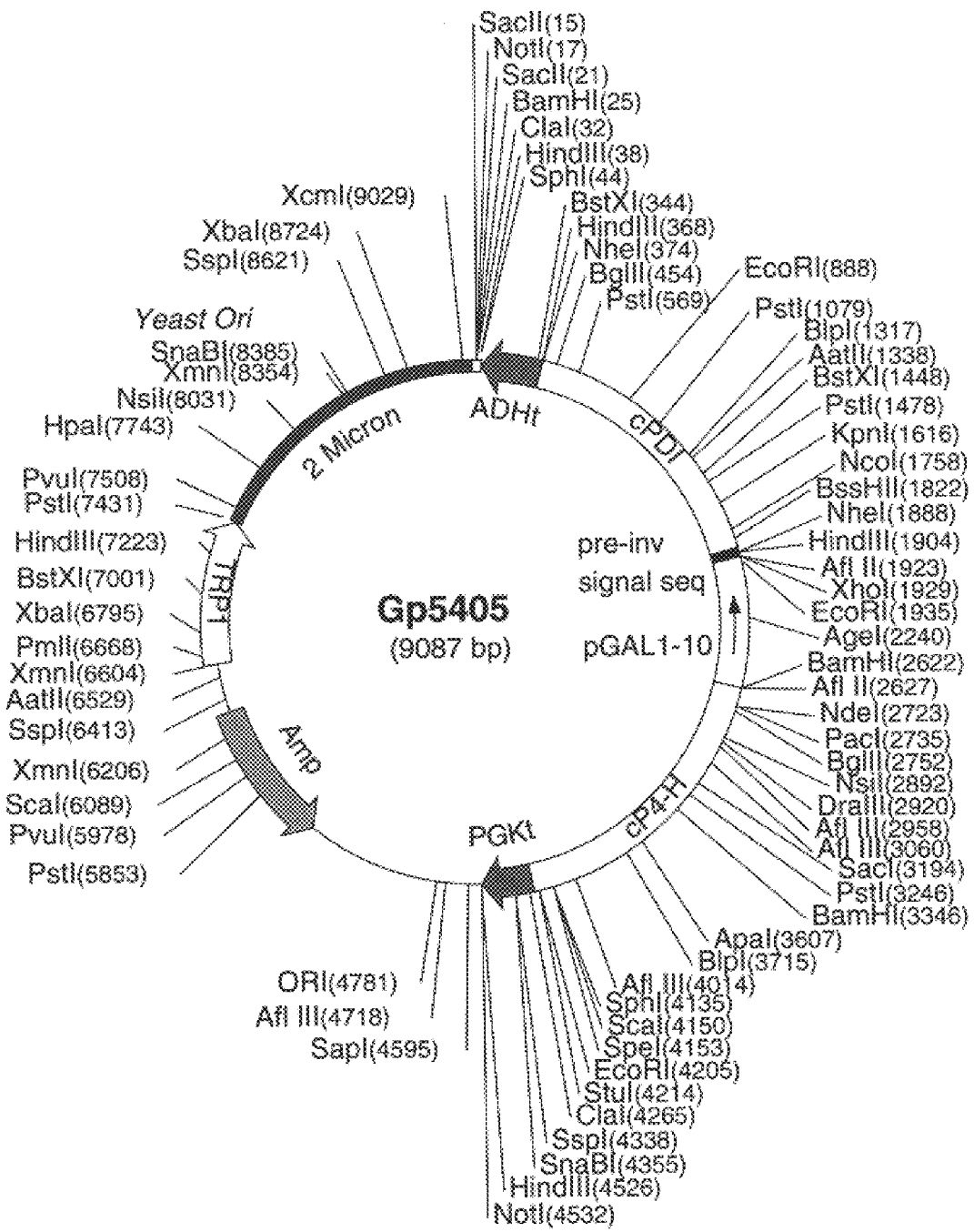
FIG. 8 illustrates the structure of plasmid Gp5405.

The entire expression unit from the Afl II to the NotI sites (from positions 723 bp to 2628 bp) was added to Gp5341 (FIG. 5) which contains the cPDI expression unit to generate plasmid Gp5403 (FIG. 7). This plasmid contains both the pre-invertase—mature cPDI—ADHt and the native cP4-H—PGKt expression units but does not contain a yeast promoter element. The yeast bi-directional GAL1–10 promoter element [M. Johnston and R. W. Davis, Mol. and Cell. Biol. (1984) 4: 1440–1448] was introduced into plasmid Gp5403 as an Afl II fragment cloned into the unique Afl II site @1923 bp (FIG. 7). The resulting plasmid, Gp5405 (FIG. 8), contains a 4515 bp NotI fragment (from positions 17 bp to 4532 bp, FIG. 8) that consists of yeast expression units for both subunits of the hydroxylation complex driven from a single, bi-directional, inducible yeast promoter element. This ensures the coordinate induction and substantially equal quantities of both subunits for the hydroxylation system in yeast.

Figure 9:
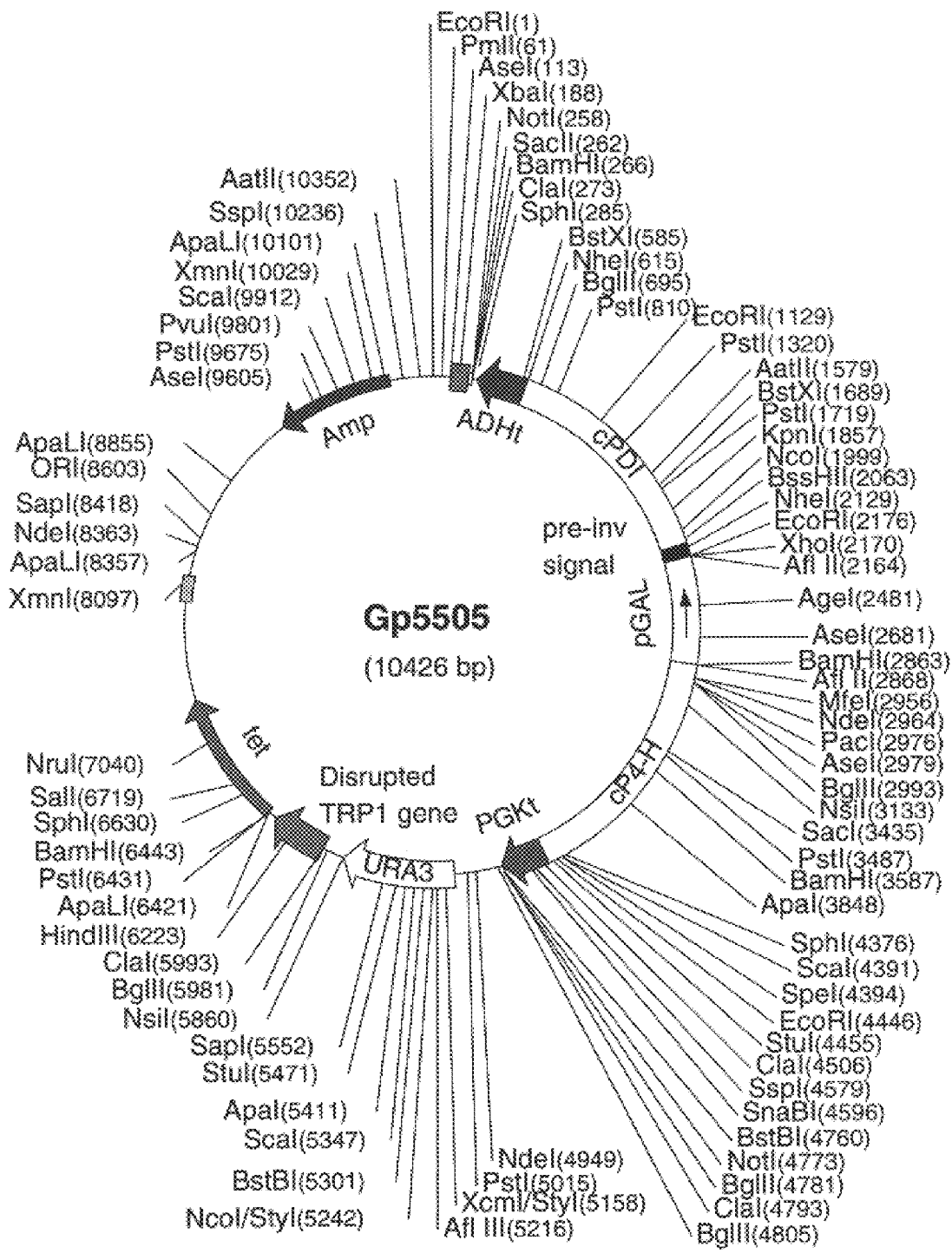
FIG. 9 illustrates the structure of plasmid Gp5505.

The final integration unit was generated by cloning the 4515 bp NotI fragment from Gp5405 into the unique NotI site (@258 bp, FIG. 4) of the TRP1 integration vector Gp5499. The resulting plasmid Gp5505, depicted in FIG. 9, was digested with PmlI (@61 bp) and ApaLI (@6421 bp) to generate a linear DNA fragment that was used to transform a Trp+ Ura– yeast strain to Ura+ Trp– upon homologous recombination into the TRP1 gene. Several transformants were selected and assayed for both cPDI and cP4-H expression to identify the desired integrated strain. The best cPDI/cP4-H producing integrant was found at a frequency of 1 in 20 Ura+ Trp– transformants and most likely represents 2 or more copies of the hydroxylation system disrupting the TRP1 gene. Other secretion signals were tried for cPDI and cP4-H; however this combination of a heterologous and a homologous secretion signal worked best to produce the most cPDI and cP4-H. Furthermore, expressing cP4-H without PDI in Saccharomyces with the expectation of forming an active enzyme complex with native yeast PDI did not reveal any detectable hydroxylation of prolines in human procollagen.

Figure 10:
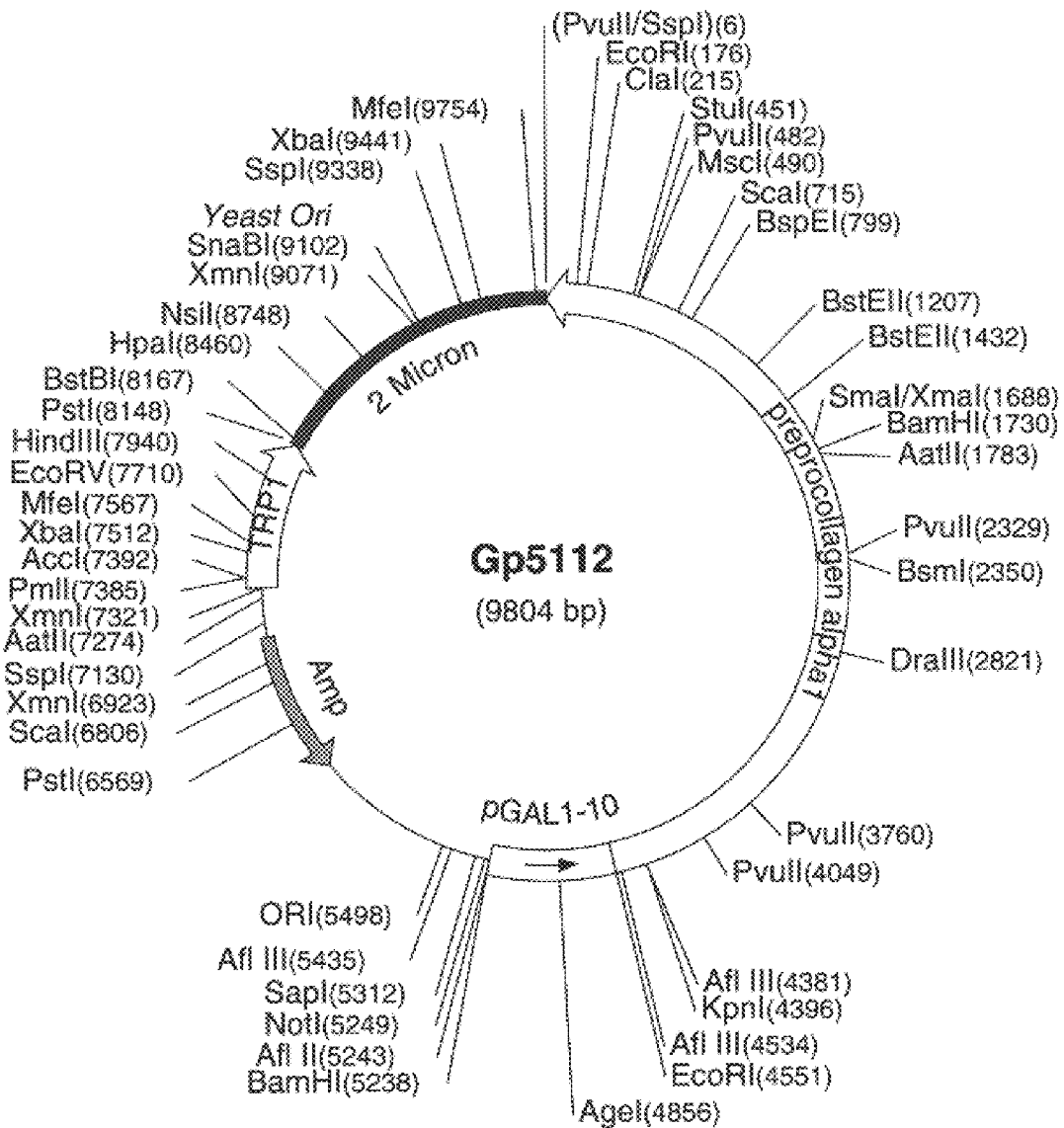
FIG. 10 illustrates the structure of plasmid Gp5112.

Example 13
Construction of Type 1 Procollagen Yeast Expression Vectors: Construction of the Type 1 Procollagen Expression Plasmid FIG. 10 depicts the starting plasmid for the dual procollagen type 1 expression plasmid. This plasmid is the basic vector Gp5020 (from the EcoRI site @4551 bp to the PvuII/SspI site @6 bp), described above, containing the coding region for the α1 chain of human type 1 procollagen [G. Tromp et al., Biochem. J. (1988) 253: 919–922] The α1 coding region unit was modified at it's 5' end by PCR in order to introduce an EcoRI site (@4551 bp, FIG. 10) just upstream of the native preprocollagen start codon (retains the native, human, secretion signal). After verification of this change by DNA sequencing the bulk of the coding region, from the original cDNA clone (from the Kpnl site @4396 bp to the PvuII/SspI @6 bp), was added to the 5' PCR fragment and the resulting construct was cloned between the PvuII and the EcoRI sites of Gp5020 to generate plasmid Gp5112 (FIG. 10). The α1 chain expression unit does not contain a transcription terminator. However, the FLP1 gene in the 2μ DNA region (from 8051 to 9707 bp, [J. L. Hartley and J. E. Donelson, Nature (1980) 286: 860 and J. R Broach and F. C Volkert, Mol. and Cell. Biol. of the Yeast Saccharomyces (1991) 1: 297–331] supplies this function.

Figure 11:
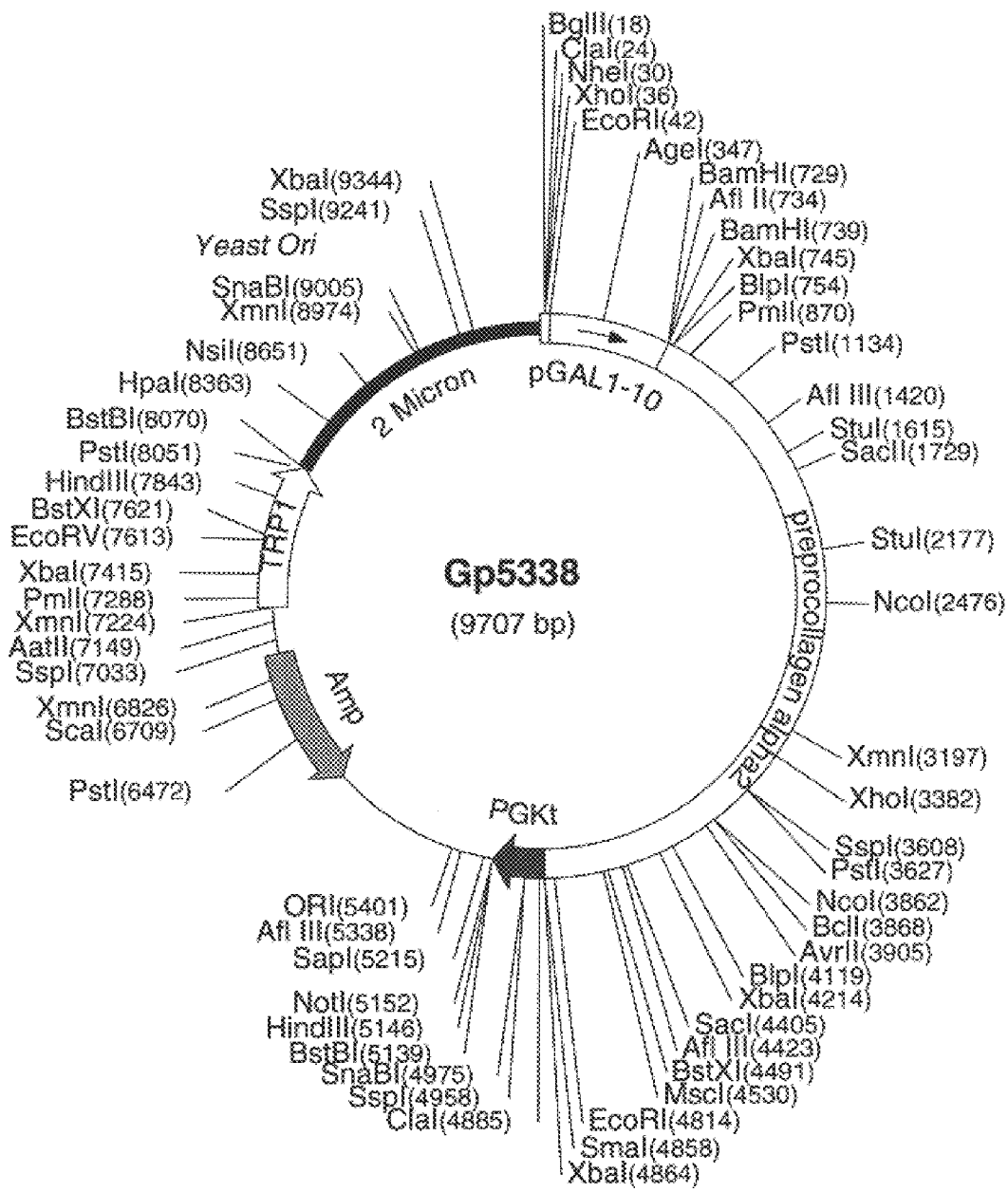
FIG. 11 illustrates the structure of plasmid Gp5338.

The expression unit for the α2 chain of human type 1 procollagen [W. d. Wet et al., J. Biol. Chem. (1987) 262: 16032–16036 and H. Kuivaniemi et al., Biochem. J. (1988) 252: 633–640] is depicted in FIG. 11. Both the 5' and the 3' ends of the original cDNA clone were modified by short PCR reactions. At the 5' end, an Afl II site (position 734, FIG. 11) was introduced upstream of the native preprocollagen start codon (retains the native, human, secretion signal). At the 3' end a BamHI site (@ position 4852, FIG. 11) was added to allow the addition of the yeast PGK transcription termination region (as a BglII–NotI fragment). After verification of both modifications by DNA sequencing, the central section of the α2 chain coding region, from the original cDNA clone, was cloned between the sequenced ends to ensure that no mutations were introduced into the coding region by the PCR reactions.

Figure 12:
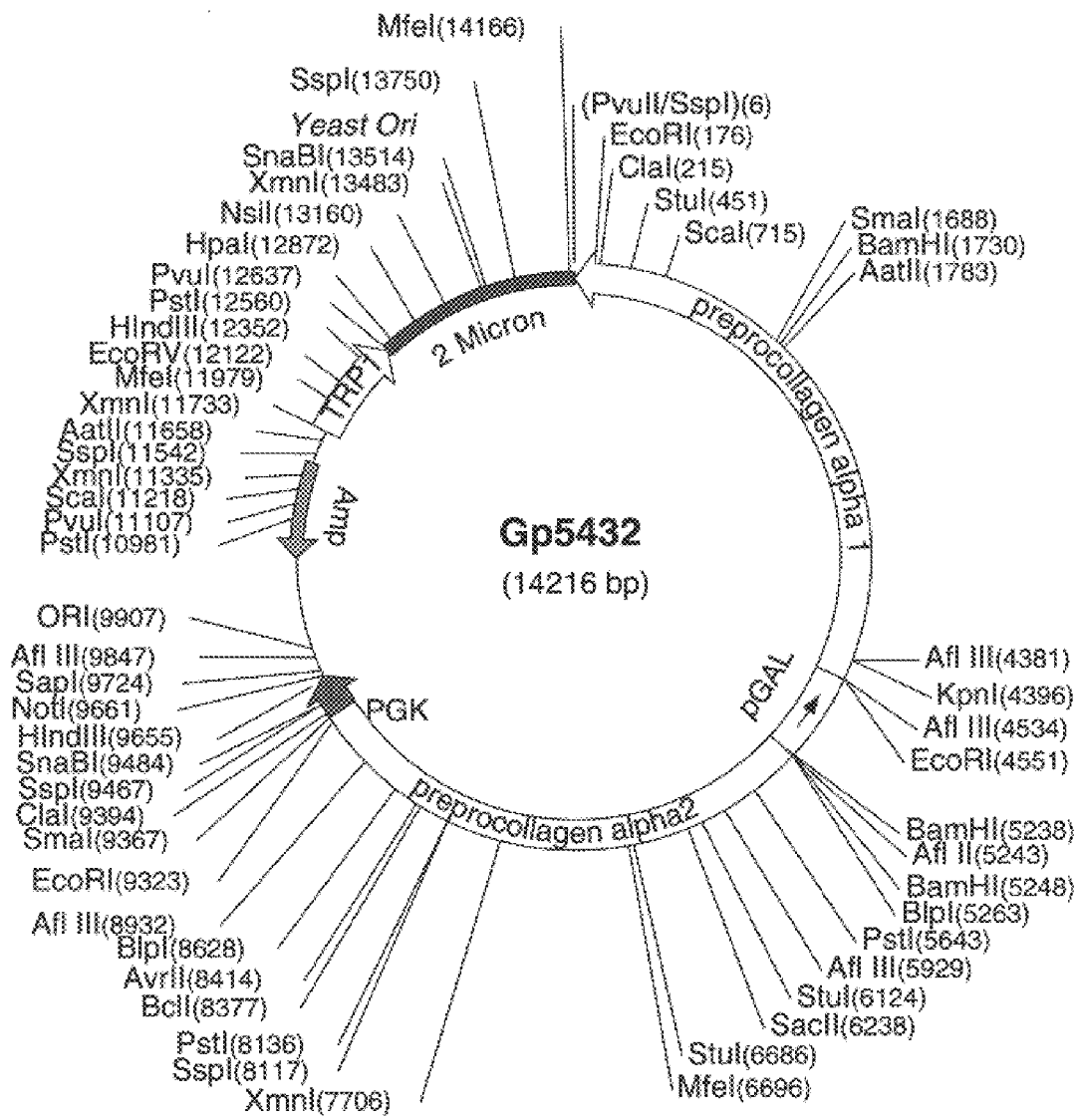
FIG. 12 illustrates the structure of plasmid Gp5432.

The type 1 procollagen expression vector, Gp5432 (FIG. 12) was constructed by adding the α2 chain expression unit (from the Afl II site @734 bp to the NotI site @5152 bp, FIG. 11) to Afl II—NotI digested Gp5112 (FIG. 10). This vector contains a yeast selectable marker, TRP1; a yeast replicator sequence, 2 micron DNA; and the human type 1 procollagen α1 and α2 chain cDNA's under the coordinate regulation of the inducible, bi-directional GAL1–10 promoter unit. This plasmid was transformed into several different yeast strains that contain the chicken hydroxylation system (cPDI and cP4-H) integrated into the TRP1 gene and hydroxylated, heterotrimeric, human procollagen was produced. Other secretion signal sequences of various types were tried on both the α1 and α2 chains; however, the above combination of native, homologous, secretion signals produced the greatest amount of heterotrimeric type 1 procollagen.

Example 14
Construction of Single Plasmid Expression System; Procollagen Plus the Hydroxylation System on a Single Plasmid To construct a single plasmid that contains both the human procollagen type1 α1 and α2 chains along with both subunits for the chicken prolyl hydroxylation system, cPDI and cP4-H, the expression units for the hydroxylation subunits had to be modified. These units needed to contain yeast promoter elements that were not homologous to each other or the GAL1 –10 promoter element and they needed yeast transcription terminators that were different from those used on the procollagen chains. This was necessary to prevent possible recombination between these elements in the final construction the result of which could generate significant plasmid instability. The starting plasmid for this construction, Gp5432 (FIG. 12) contains a unique NotI site @9661 bp and a unique SapI site @9724 bp that would be useful for the introduction of the hydroxylation subunits. Therefore the subunit expression cassettes also need to have the appropriate ends to be able to be cloned into the indicated sites.

Figure 13:
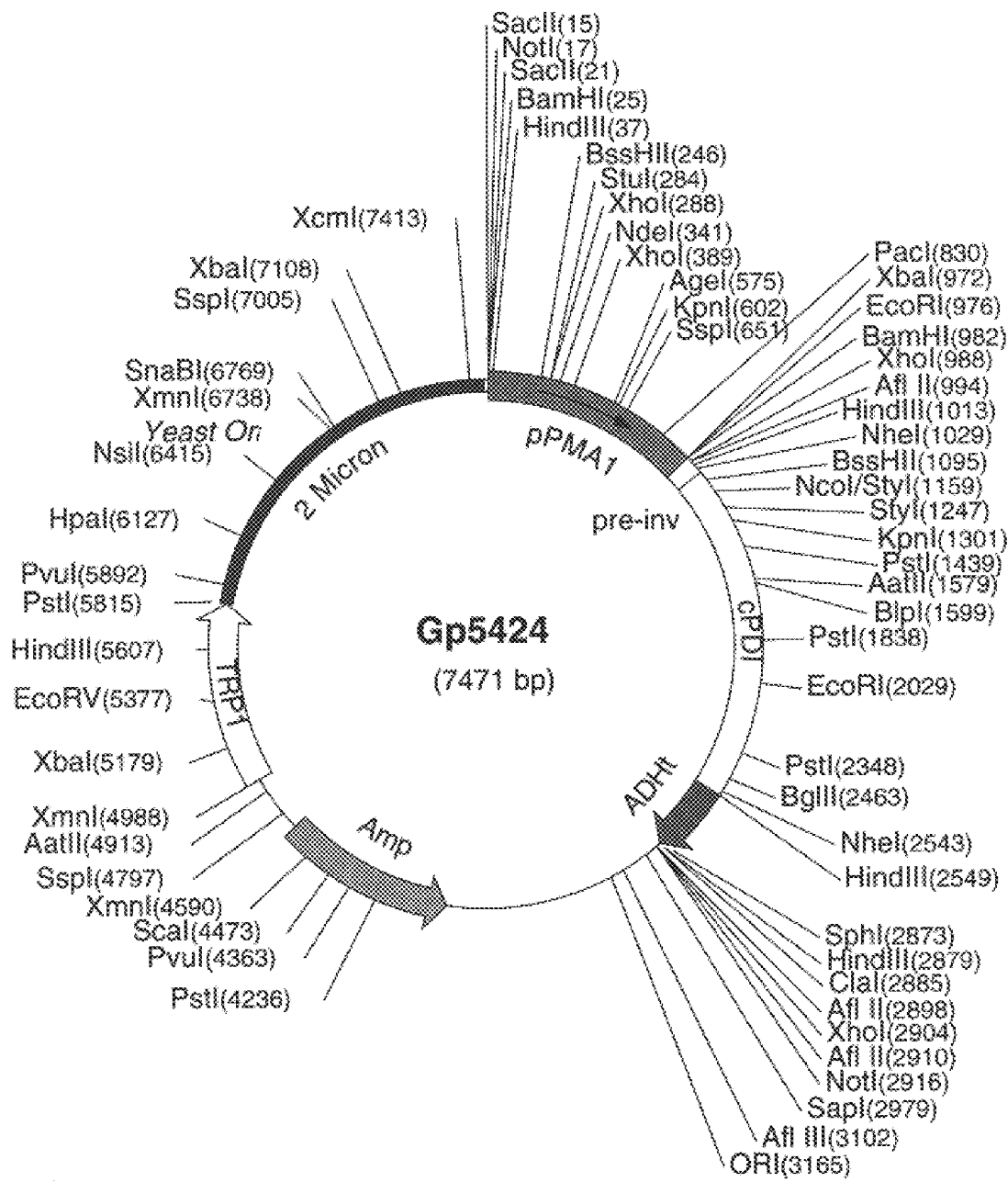
FIG. 13 illustrates the structure of plasmid Gp5424.
Figure 14:
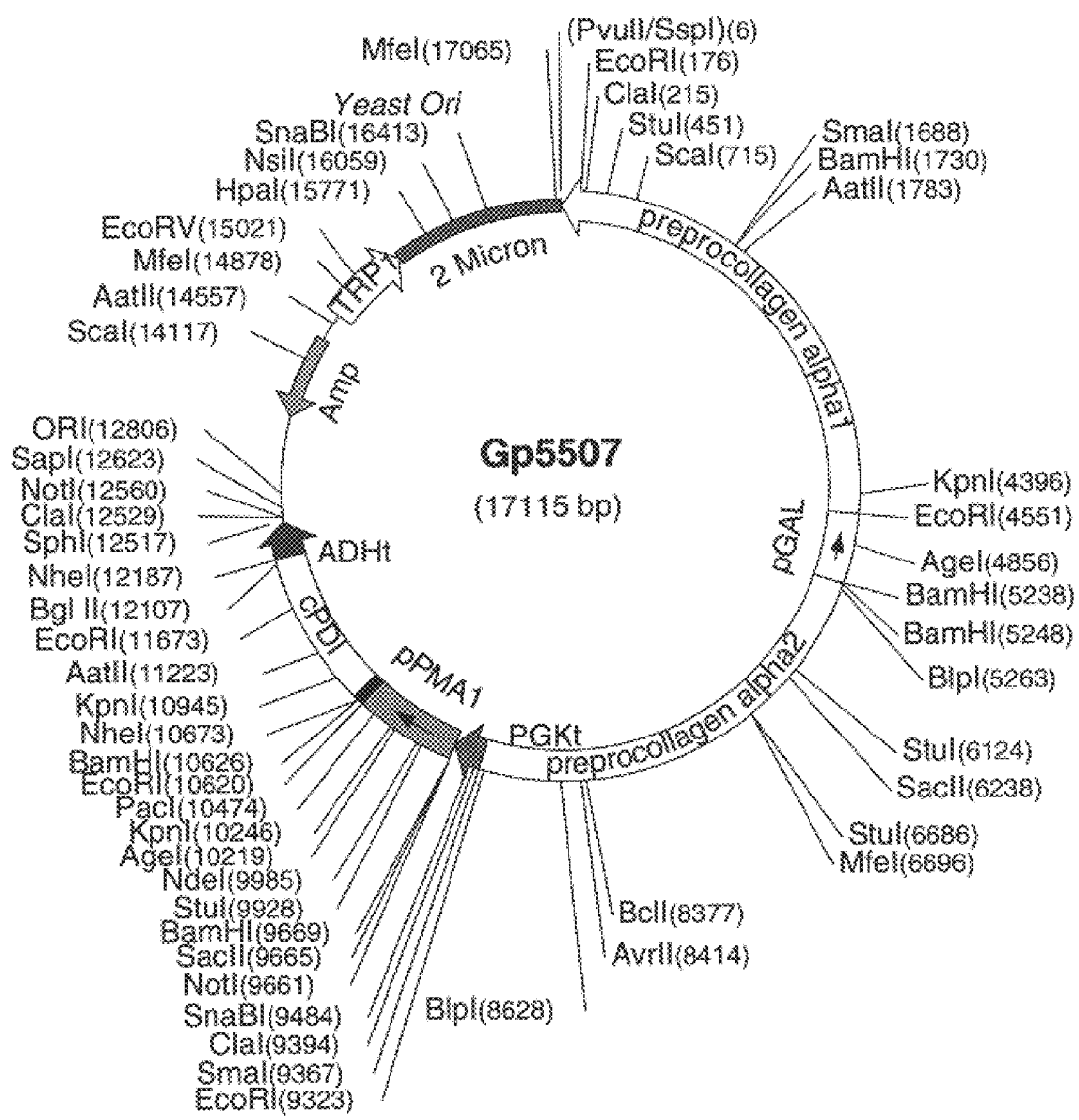
FIG. 14 illustrates the structure of plasmid Gp5507.

Plasmid Gp5424 (FIG. 13) depicts the modified cPDI expression unit. This plasmid contains our basic vector, Gp5020, sequences from the NotI site @2916 bp to the PvuII site @6 bp. The polylinker and GAL1–10 promoter element that compromises the rest of the basic vector has been removed and replaced with altered polylinker sequences to introduce a second NotI site (@17 bp). The pre-invertase—mature cPDI—ADHt fragment (from the EcoRI site @976 bp to the ClaI site @2885) is identical to that described in Gp5341 (FIG. 5) above. The yeast promoter element had been changed to the constitutively regulated plasma membrane ATPase (PMA1, [R. Serrano, et al., Nature (1986) 319: 689–693]) promoter element. This promoter fragment (from the BamnH site @25 bp and the EcoRI site @976 bp) was generated by PCR, and its functionality tested prior to introduction into this plasmid. The resulting 2899 bp NotI fragment (from site @17 bp to site @2916, FIG. 13) containing the pPMA1—pre-invertase—mature cPDI—ADHt expression unit was cloned into the unique NotI site in Gp5432 (@9661 bp, FIG. 12) to produce the intermediate plasmid Gp5507 depicted in FIG. 14. The cPDI expression unit was cloned such that it's direction of transcription was away from the procollagen α2 chain.

Figure 15:
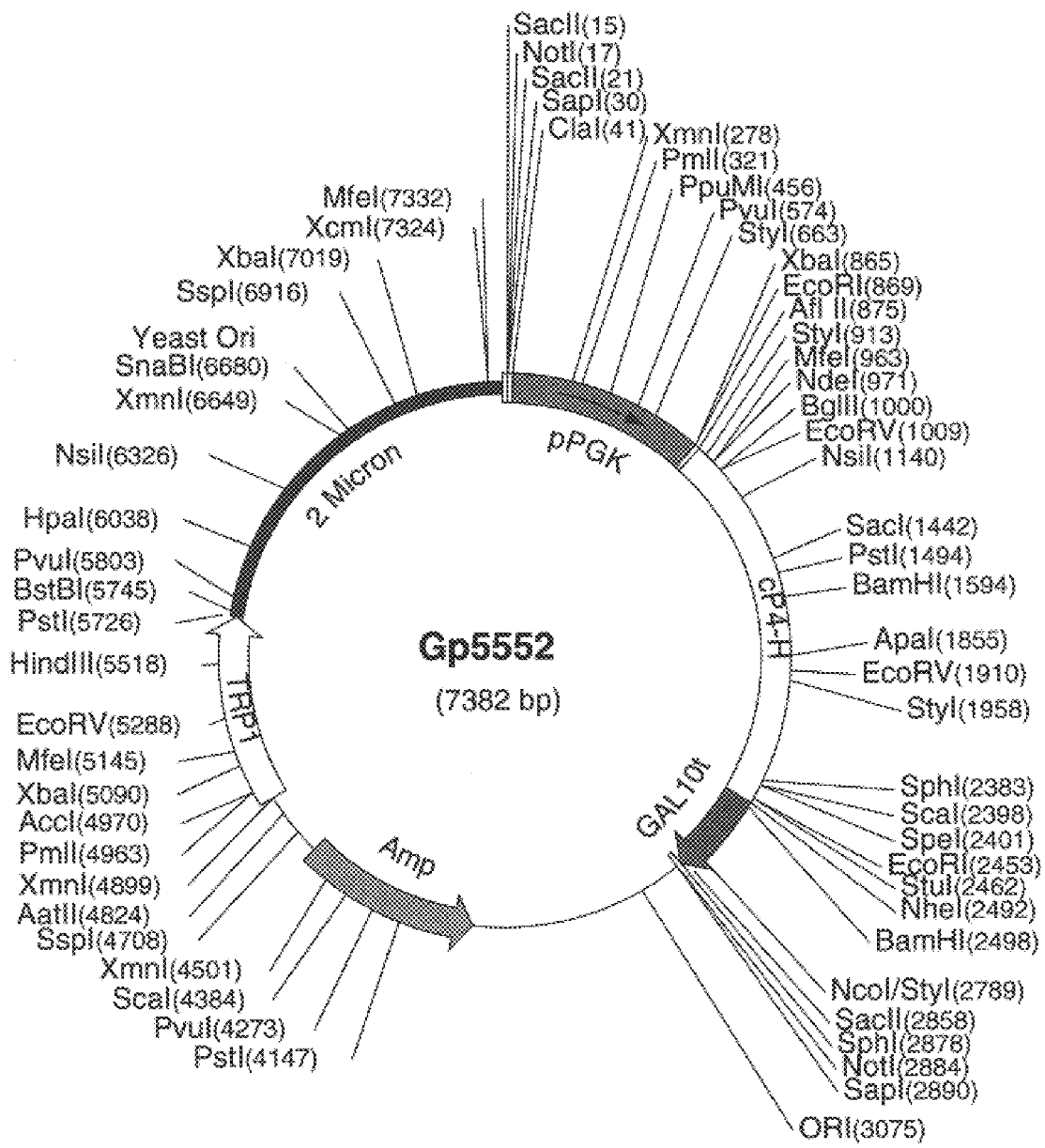
FIG. 15 illustrates the structure of plasmid Gp5552.

The structure of the modified cP4-H expression unit is depicted in FIG. 15. This plasmid (Gp5552) contains our basic vector, Gp5020, sequences from the NotI site @2884 bp to the PvuII site @6 bp. The polylinker and GAL1–10 promoter element that comprise the rest of the basic vector has been removed and replaced with altered polylinker sequences to introduce a second NotI site (@17 bp) as well as a second SapI site (@30 bp). This unit contains the constitutively regulated phosphoglycerate kinase gene [R. A. Hitzeman et al., Nucleic Acids Res. (1982) 10: 7791–7808] promoter element (from ClaI site @41 bp to EcoRI site @869 bp) connected to the modified cP4-H coding region (from the Afl II site @875 bp to the NheI site @2492 bp) described in FIG. 6 above. The transcription terminator in this unit is from the yeast GAL10 gene [S. John and R. Davis, J. Mol. Biol. (1981) 152: 285–315 and S. John et al. J. Mol. Biol. (1981) 152: 317–334] and extends from the NheI site @2492 bp to the SphII site @2878 bp.

Figure 16:
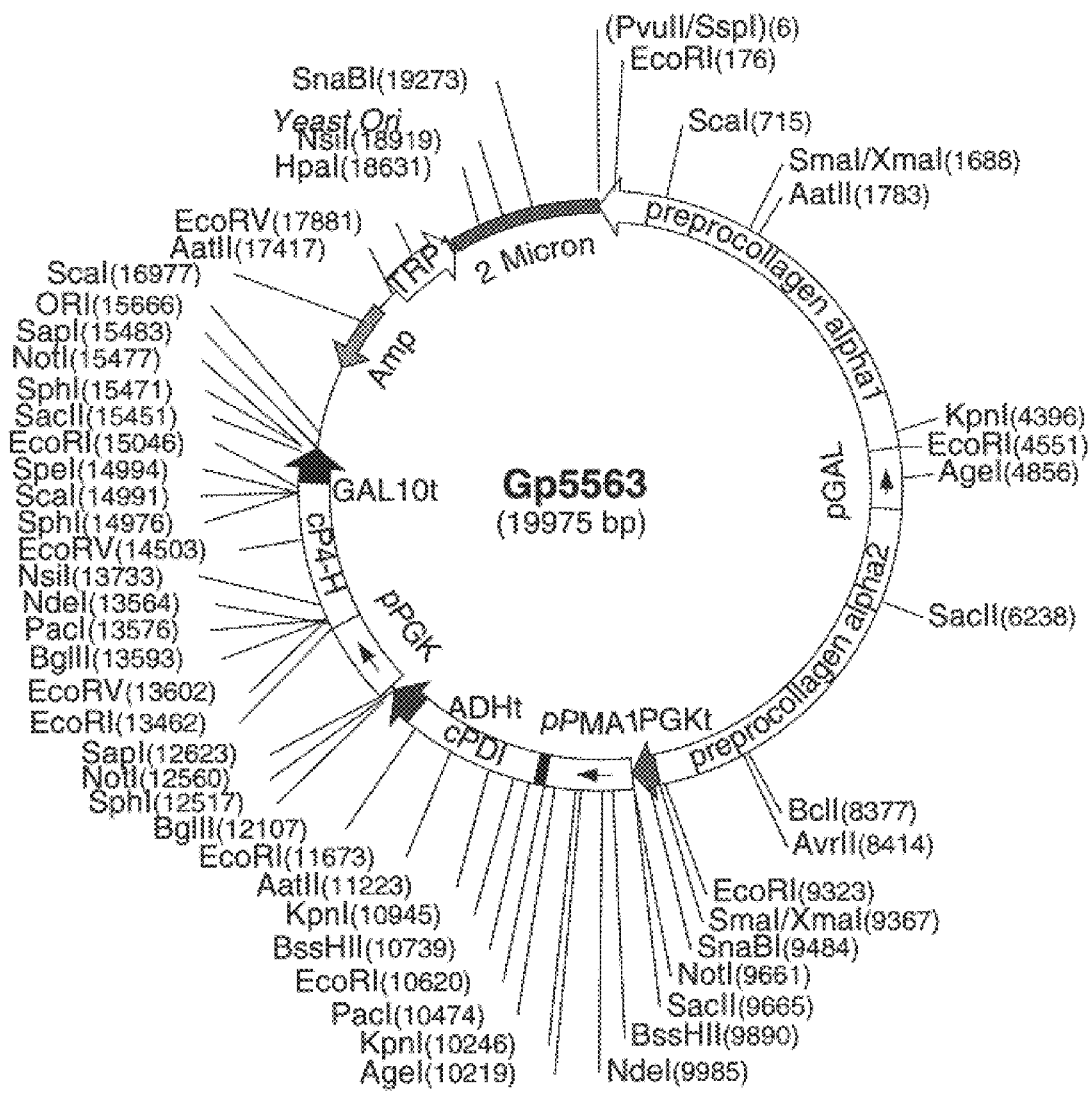
FIG. 16 illustrates the structure of plasmid Gp5563.

The final expression vector was completed by cloning the 2860 bp SapI fragment from Gp5552 (FIG. 15) into the unique SapI site (@12623 bp, FIG. 14) of plasmid Gp5507. Since the SapI recognition site is not palindromic but directional there is only one possible product from this ligation (Gp5563) which is depicted in FIG. 16. This plasmid contains the coordinately regulated, inducible, human procollagen α1 and α2 expression unit along with a constitutively expressed chicken hydroxylation system (cPDI/cP4-H). All the genes have different yeast promoter elements as well as different transcription terminators. This plasmid was transformed into various yeast strains for analysis of heterotrimeric, hydroxylated procollagen expression.

Figure 17:
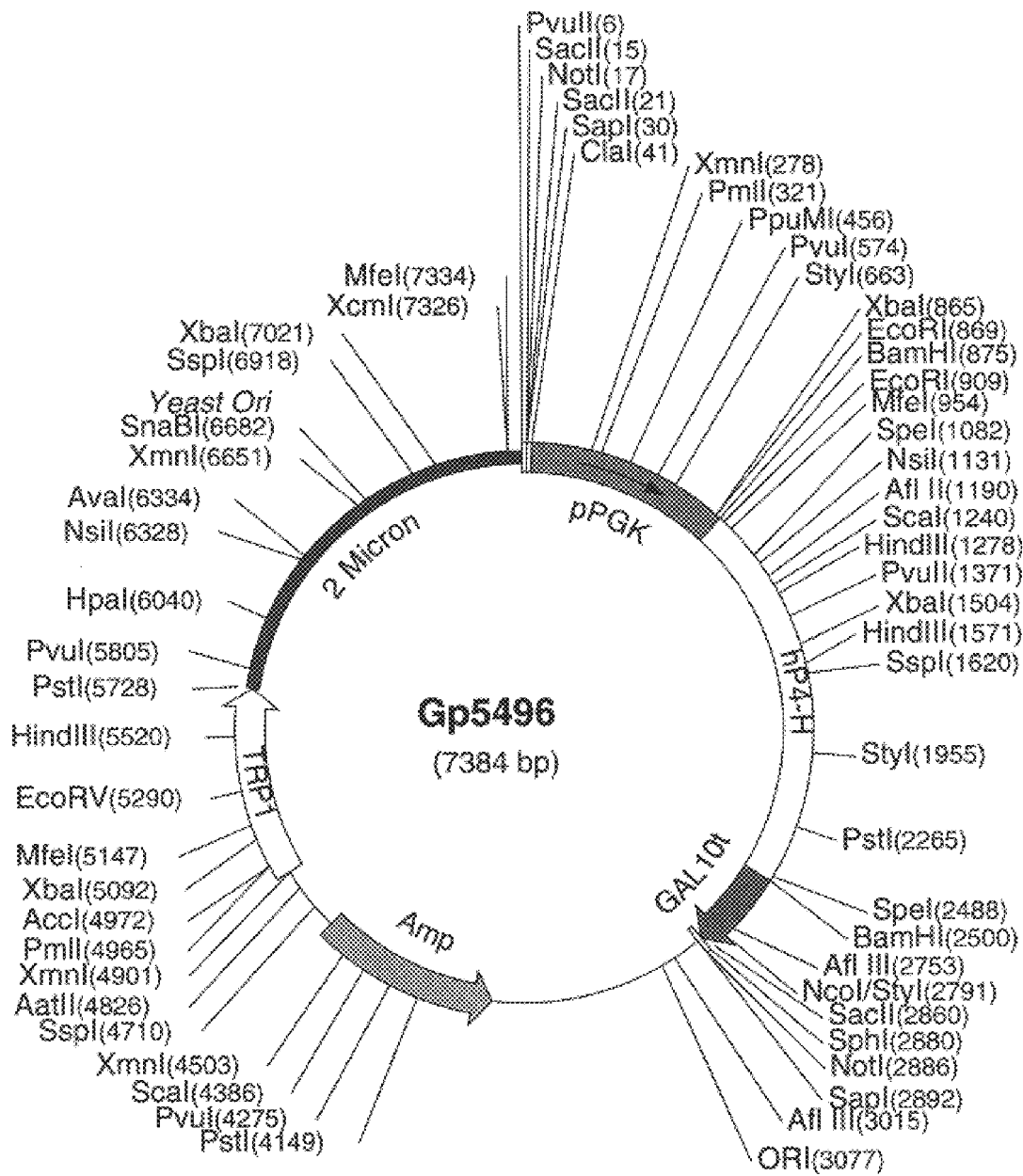
FIG. 17 illustrates the structure of plasmid Gp5496.
Figure 18:
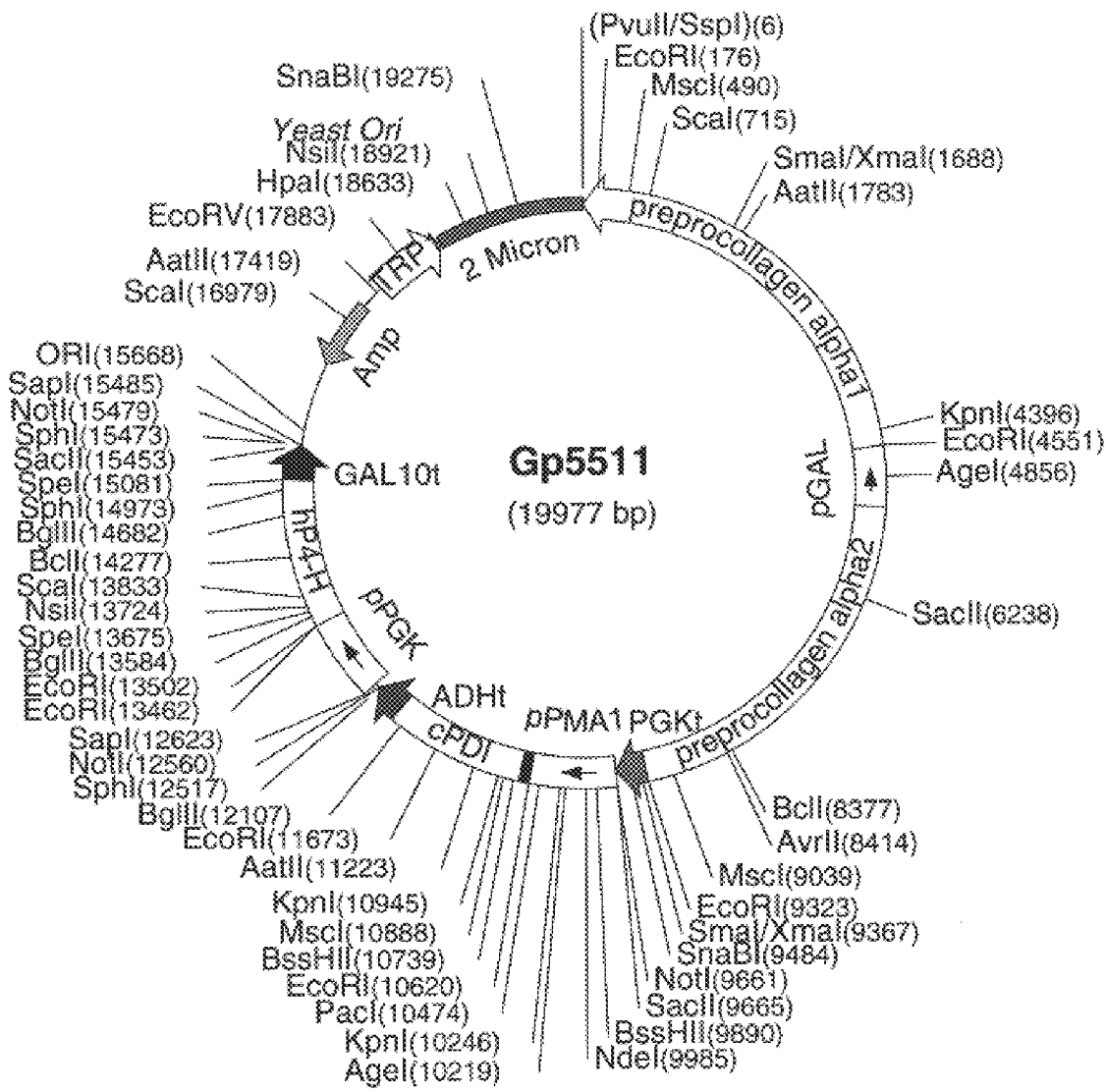
FIG. 18 illustrates the structure of plasmid Gp5511.

The genes for the human hydroxylation system were tested by introducing them into plasmid Gp5432 (FIG. 12) as was done for the chicken genes. The first gene tested was the human prolyl 4-hydroxylase subunit (hP4-H) [T. Helaakoski et al., Proc. Natl. Acad. Sci. USA (1989) 86: 4392–4396]. The cDNA for the hP4-H gene, generated by PCR and verified by DNA sequencing, had been modified to include BamHI sites at both ends of the native coding region (the native human secretion signal was left intact as with the cP4-H expression unit as described above). The hP4-H BamHI fragment was cloned between the yeast PGK promoter element and the yeast GAL10 transcription terminator element to generate plasmid Gp5496 (FIG. 17). This plasmid contains a 2862 bp SapI fragment (from site @30 bp to site @2892 bp) which contains the pPGK—native hP4-H - GAL10t expression unit that was cloned into the intermediate plasmid Gp5507 (FIG. 14) which already contains the cPDI gene in the NotI site as well as the inducible procollagen expression unit. The resulting plasmid, Gp5511 (FIG. 18), was transformed into yeast for analysis of heterotrimeric, hydroxylated procollagen expression. The unique feature of this plasmid is that the hydroxylation system expressed is a hybrid of the chicken PDI subunit with the human P4-H subunit. Since the cPDI/cP4-H hydroxylation system has been shown to work, the activity of the hP4-H cDNA can be ascertained with a functional cPDI/hP4-H hybrid system.

Figure 19:
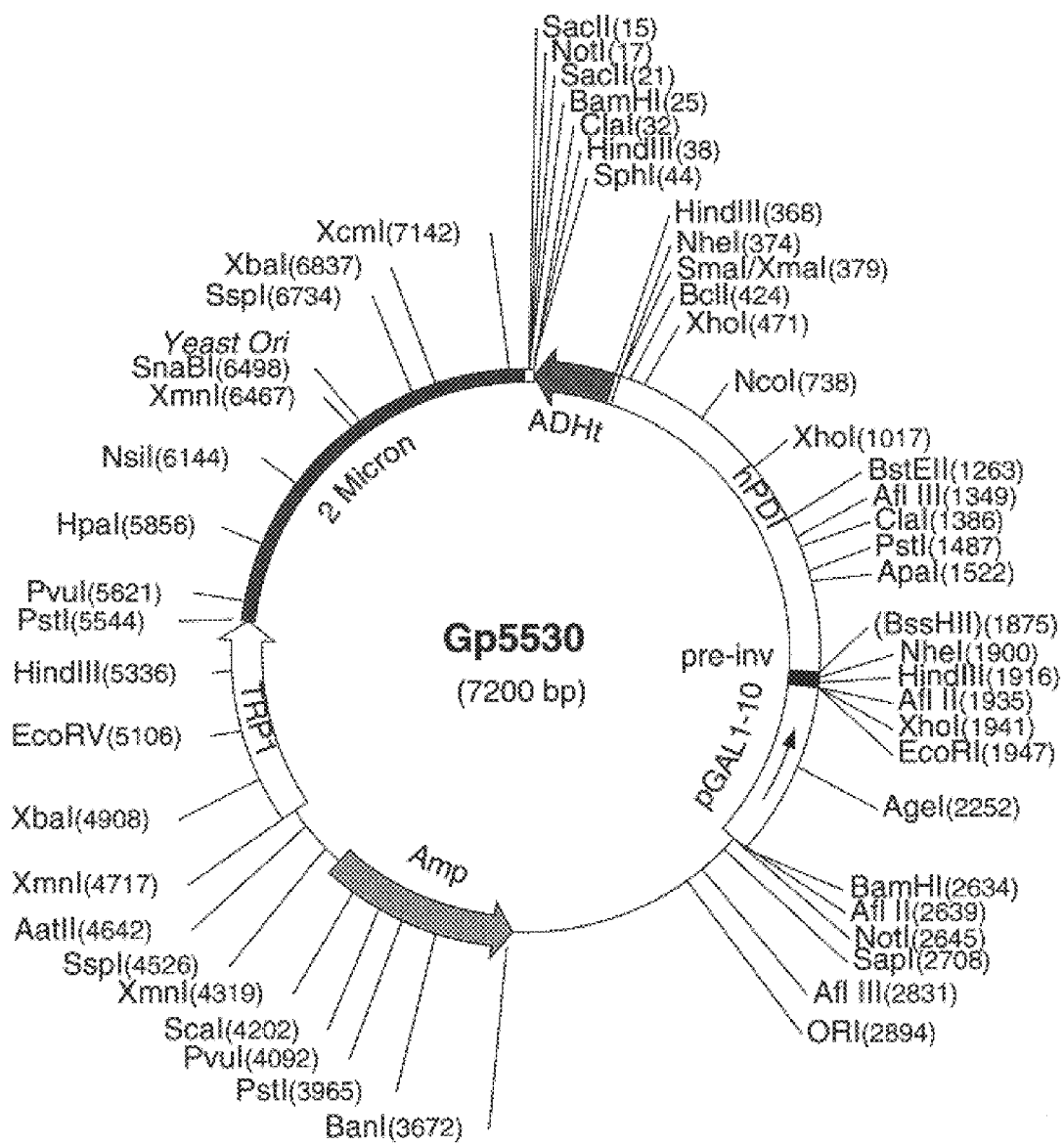
FIG. 19 illustrates the structure of plasmid Gp5530.
Figure 20:
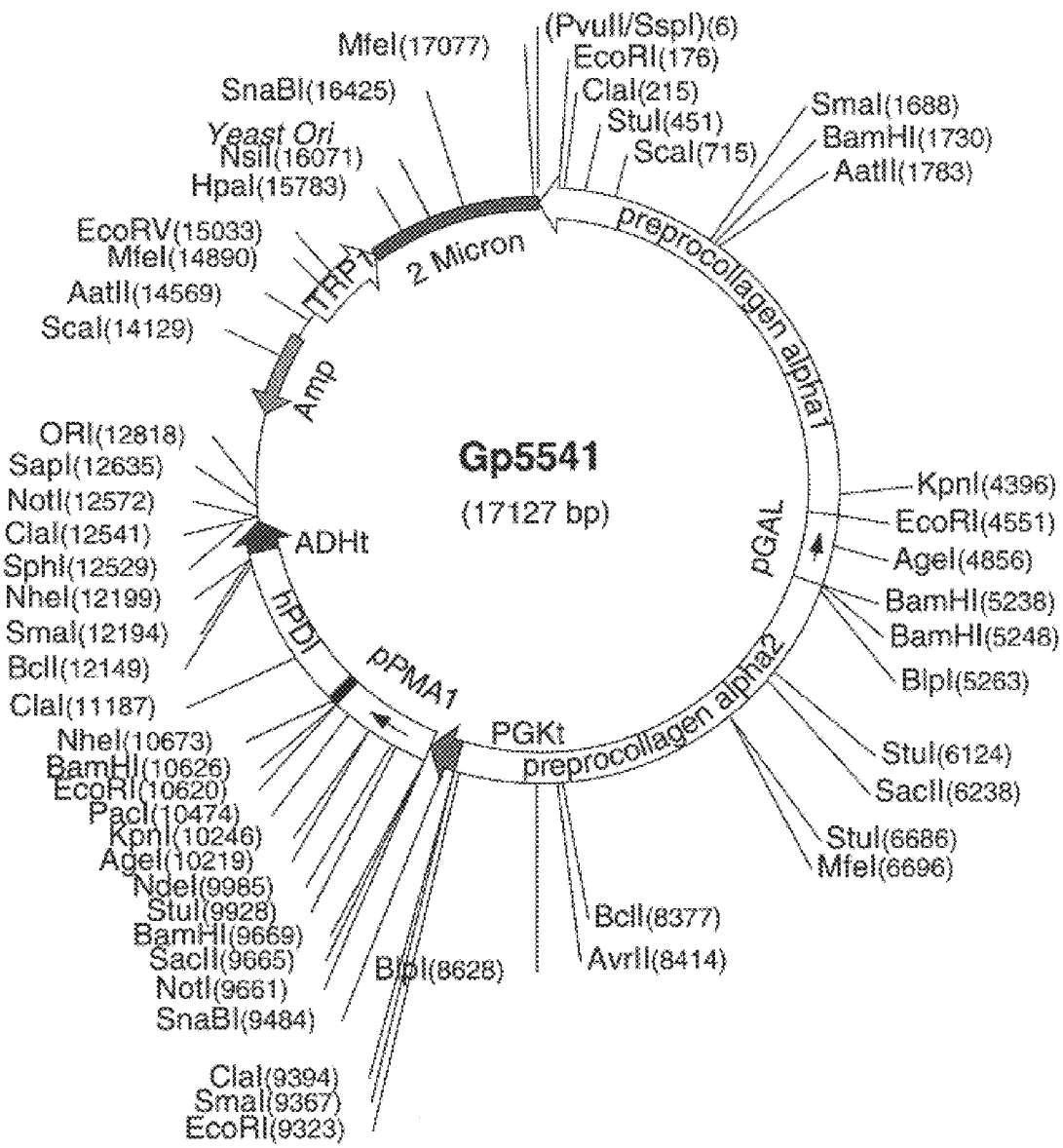
FIG. 20 illustrates the structure of plasmid Gp5541.
Figure 21:
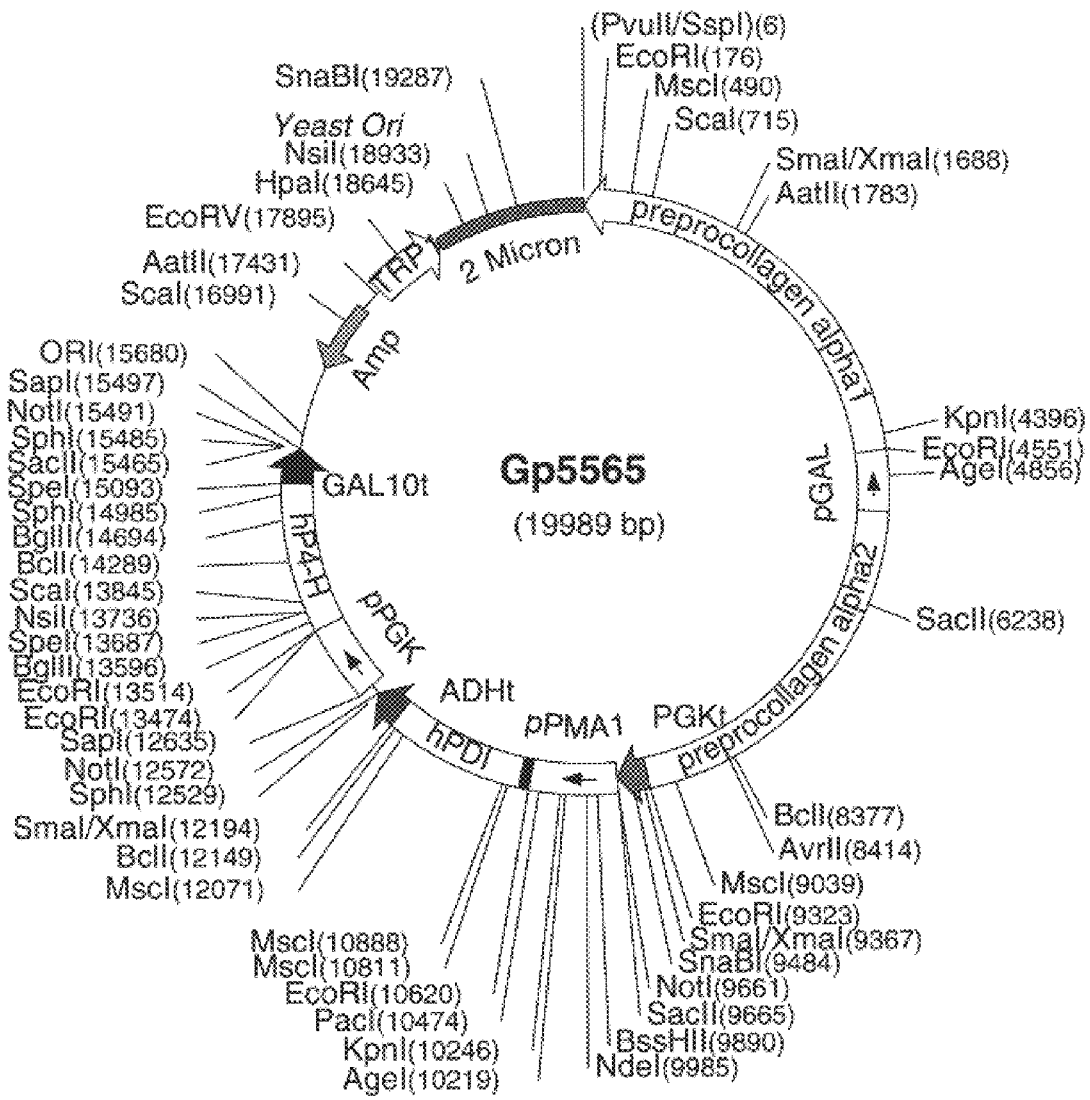
FIG. 21 illustrates the structure of plasmid Gp5565.

In addition to the cPDI/cP4-H and the cPDI/hP4-H system plasmids the hPDI/hP4-H system was also constructed for evaluation. Toward this end the human protein disulfide isomerase gene [T. Pihlajaniemi et al. EMBO J. (1987) 6: 643–649] was cloned by PCR and its DNA sequenced determined. The PCR reaction introduced modification at both ends of the gene identical to those described above for the cPDI clone in plasmid Gp5341 (FIG. 5). The 5' end was modified to allow fusion of the mature coding sequence with the yeast pre-invertase secretion signal sequence such that the normal signal peptidase site was left intact. The 3' end was modified to introduce a NheI site just downstream of the normal translation stop codon. The pre-invertase—mature hPDI fragment was cloned between the yeast GAL1–10 promoter element and the ADH transcription terminator element to generate plasmid Gp5530 (FIG. 19). This configuration allows the isolation of a 1526 bp NheI fragment extending from the NheI site in the pre-invertase secretion signal (@1900 bp) to the 3' end of the coding region (@374 bp). This fragment was used to replace the identical NheI fragment for the cPDI gene in plasmid Gp5507 (FIG. 14 sites 10673 bp to 12187 bp) to generate plasmid Gp5541 (FIG. 20). To complete the hPDI/hP4-H expression plasmid the hP4-H SapI fragment from Gp5496 (FIG. 17) was added to Gp5541 to generate plasmid Gp5565 (FIG. 21). This plasmid was transformed into various yeast strains for analysis of heterotrimeric, hydroxylated procollagen expression.

Example 15

Results of Heterotrimeric Hydroxylated Procollagen Production

Plasmids Gp5563 (FIG. 16), cPDI/cP4-H hydroxylation system, Gp5511 (FIG. 18), cPDI/hP4-H hybrid hydroxylation system, and Gp5565 (FIG. 21), hPDI/hP4-H hydroxylation system, were transformed into yeast and analyzed for the production of hydroxylated, heterotrimeric type 1 procollagen. Plasmid Gp5511 (cPDI/hP4-H) generated the first hydroxylated type 1 (α1α2) procollagen expressed in yeast. Plasmid Gp5563 (cPDI/cP4-H) was also found to produce levels of hydroxylated heterotrimeric procollagen equal to that found with plasmid Gp5511. This result indicates that the hP4-H cDNA clone makes active protein that can fully substitute for the cP4-H to form active hydroxylation tetramer with the cPDI subunit. However, the hPDI/hP4-H expression plasmid Gp5565, generated much lower levels (as much as three times lower) of hydroxylated, heterotrimeric procollagen than did either of the other plasmids tested (all in the same yeast strain). This might be due to some limitation of the activity of the hPDI/hP4-H tetrameric complex in yeast or possibly the activity/structure of the protein encoded by the hP4-H cDNA since we know the hP4-H subunit appears to work as well as the cP4-H subunit (Gp5511 vs Gp5563 results). Also, it could be that substitution of a different heterologous secretion signal could increase production of hydroxylated heterotrimer. Plasmid stability studies on transformants containing expression plasmid Gp5511 (cPDI/hP4-H) indicated a high degree of plasmid loss (up to 85% of cells showing loss of plasmid under culture conditions) especially upon induction of gene expression by galactose.

Example 16

Construction of a Two-Plasmid Expression System

Figure 22:
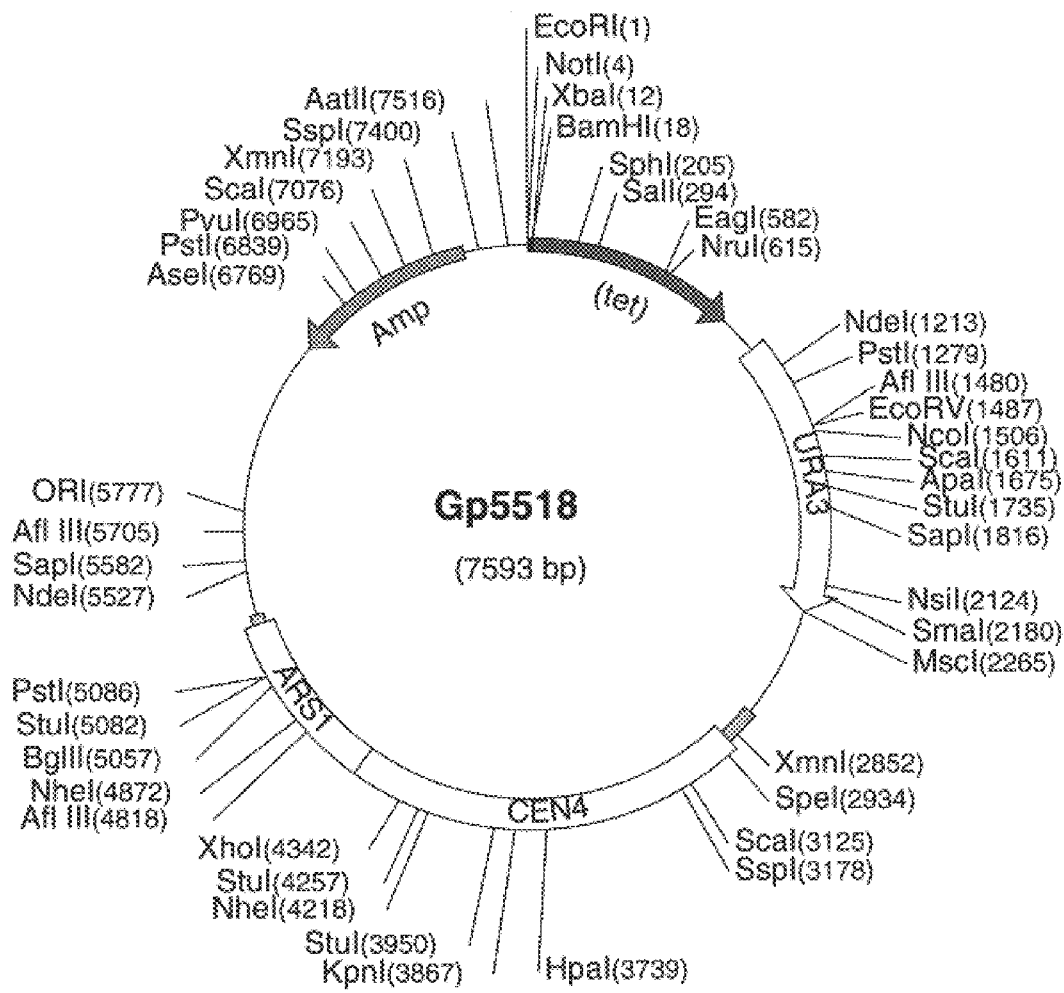
FIG. 22 illustrates the structure of plasmid Gp5518.

Another way to produce hydroxylated, heterotrimeric procollagen in yeast would be to use a two plasmid system with the procollagen chains on a high copy number (2 Micron replicator) plasmid and the hydroxylation subunits on a low copy number, CEN4 ARS1 plasmid such as YCp50 [M. D. Rose et al., Gene (1987) 60: 237–243]. The procollagen α1 and α2 chains are already on a high copy number plasmid, Gp5432 (FIG. 12) described above. To put the chicken hydroxylation system onto a low copy number plasmid a polylinker was added to plasmid YCp50 between the EcoRI site (@1 bp) and the BamHI site (@375 bp) to generate plasmid Gp5518 as depicted in FIG. 22 and Table 4.

TABLE 4

Oligonucleotides GN399 and GN398

```
              EcoRI   NotI      XhoI    BamHI
GN399 5'      AATTC   GCGGCCGC  TCTAGA  G        3'
(SEQ ID NO:8)
GN398 3'              G         CGCCGGCG AGATCT CCTAG 5'
(SEQ ID NO:9)
```

Figure 23:
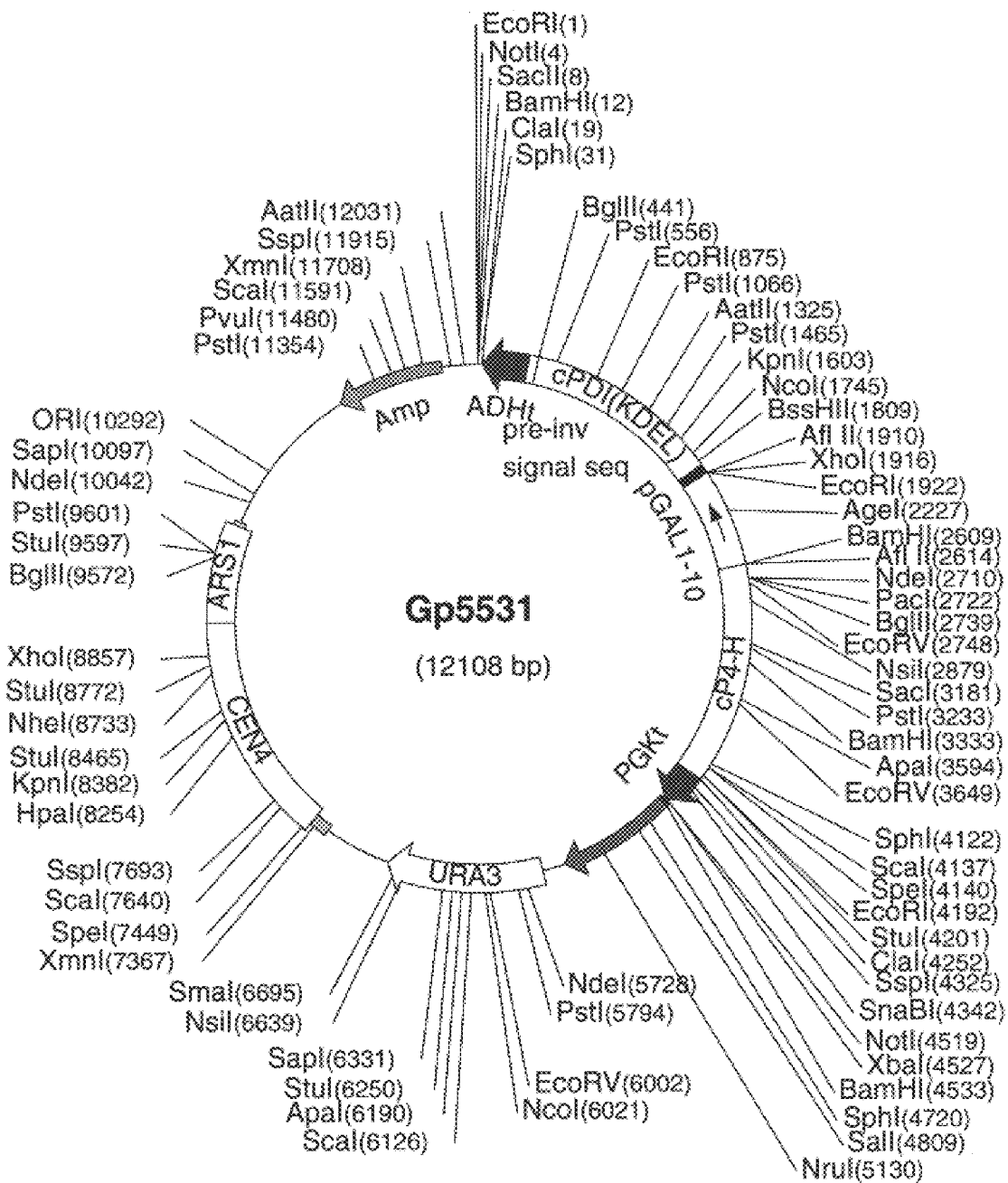
FIG. 23 illustrates the structure of plasmid Gp5531.

This polylinker introduced a unique NotI site (@4 bp, FIG. 22) in the Tet gene region of YCp50. The chicken hydroxylation system, on a single 4515 bp NotI fragment from plasmid Gp5405 (from site @17 bp to site @4532 bp, FIG. 8) described above was cloned into this NotI site to generate the expression plasmid Gp5531 (FIG. 23). This plasmid could be introduced using the URA3 gene as the yeast selectable marker. Trp– Ura– yeast were transformed to Trp+ Ura+ using plasmids Gp5432 (FIG. 12) and Gp5531 (FIG. 23) to generate prototrophic strains that could be grown in fermentors. Transformants containing the two plasmid system produced hydroxylated, heterotrimeric type 1 procollagen, at levels similar to those observed in the strains containing the integrated chicken hydroxylation system and plasmid Gp5432 only. The transformants also appeared stable with little detectable loss of either plasmid during culturing. KDEL (mammalian) versus HDEL (yeast perferred) ER retention amino acids on preInv-mature cPDI proved similar in heterotrimer production in the two different systems above.

Example 17
Integration of the α1/α2 (I) Procollagen Expression System

Figure 25:
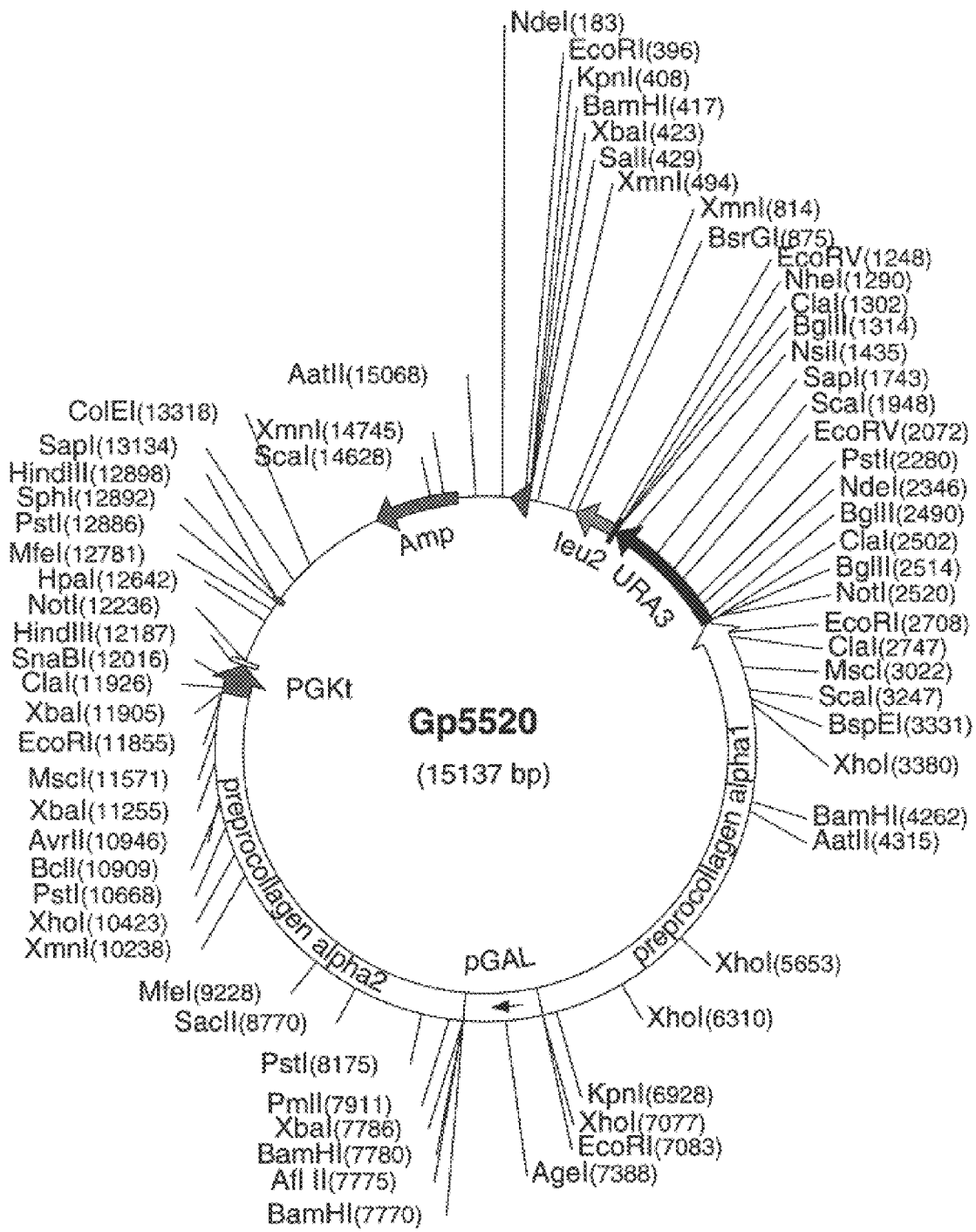
FIG. 25 illustrates the structure of plasmid Gp5520.

To determine if a single copy would express higher amounts of heterotrimer than GP5432 (FIG. 12, a high copy number plasmid) we constructed GP5520 as shown in FIG. 25, which contains a leu2 disruption that contains the URA3 gene and the α1/α2 (I) procollagen expression units under GAL1–10 promoter control. The NotI fragment in FIG. 25 is oriented so α1(I) procollagen can use the URA3 transcription termination signals when put into the chromosome since the NotI fragment containing these genes does not have a termination region on a α1(I) procollagen.

Transplacement of the HpaI to SalI fragment into the chromosome was done by transforming the plasmid after cutting with these two enzymes. Eleven Ura+leu– transformants were examined for levels of heterotrimer produced at 20° C. The Westerns of α1(I) procollagen using antibody LF-39 shows no detectable amounts of α1(I) procollagen protein in these transformants, while controls showed normal amounts as expected.

Example 18
Gal1 Deletion

Figure 26:
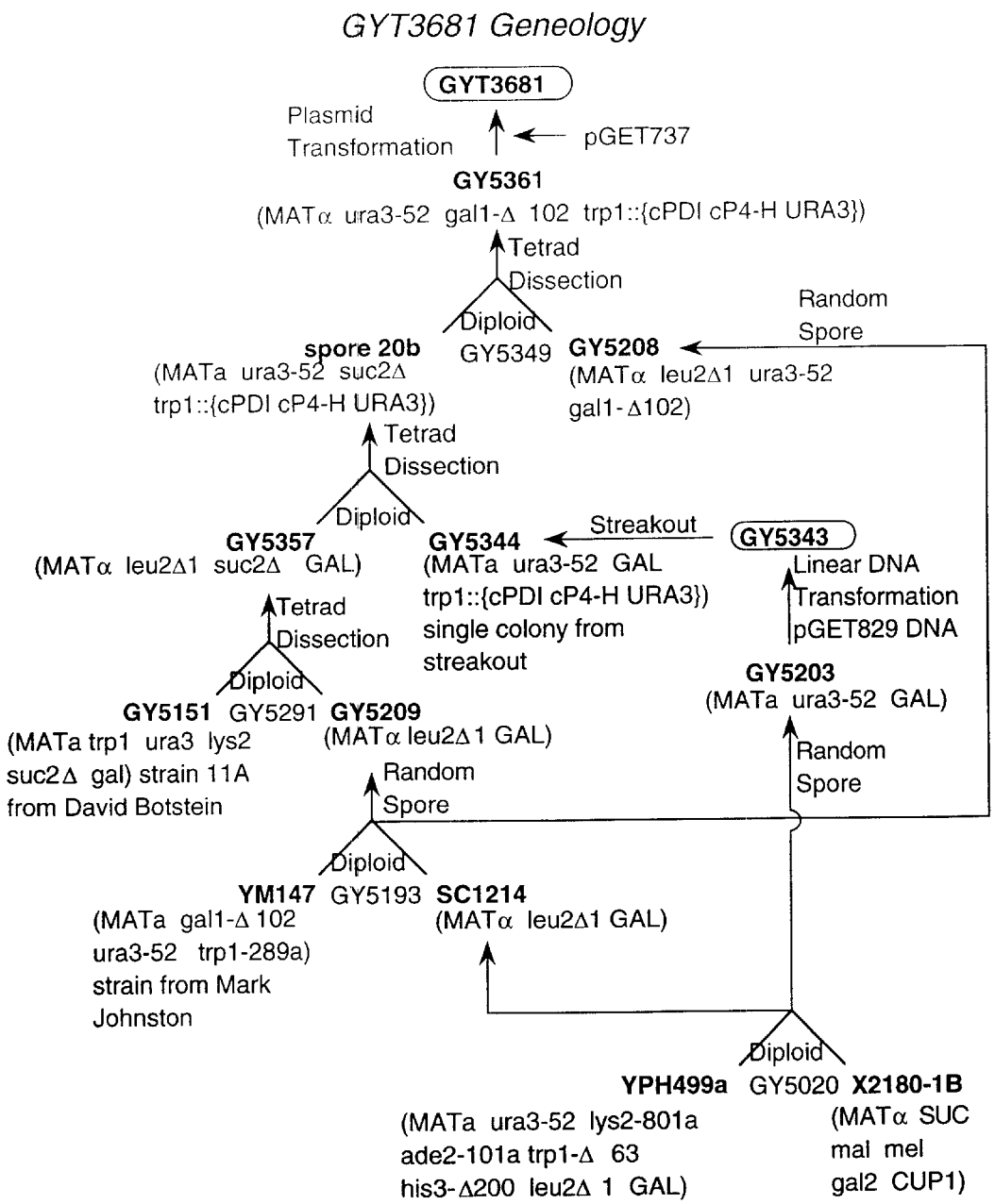
FIG. 26 illustrates the construction of plasmid GYT3681 (pGET737=Gp5432).

A Gal1 deletion, GYT3681, was constructed as shown in FIG. 26. This deletion allows for growth on minimal glucose with nonmetabolized galactose present as an inducer.

Example 19
Yeast Fermentation and Cell Breakage

Yeast media consisted of 2×YNB media (0335-15-9; Difco Laboratories, Detroit, Mich.), 40 g/L glucose, 0.5% galactose (for induction) and 0.5% casein amino acids (0231-17-2; Difco Laboratories) at pH 6.5. 6 liters of media was innoculated with a GYT3681 starter culture to OD 0.1 in a 15 liter Biostat C fermenter (Braun Biotech International, Germany) and grown at 30° C. using 20% saturated air. Temperature, pH and air were maintained throughout the fermentation. 0.6 liters of 10×YNB media with 200 g/L glucose was added when the culture reached an OD of 9–10. The culture was grown to OD of 25 and harvested.

The yeast suspension was stored overnight at 4° C. with the yeast cells settling to the bottom of the container. The supernatant was removed and the cells diluted 1: 10 with 0.1 M Tris, 0.4 M NaCl at pH 7.5. 500 g of 0.5–0.7 mm glass beads were loaded into a Dyna-Mill TypKDL A cell disrupter (Willy A. Bachofen, Basel, Switzerland). The cell disrupter was set 2000 rpm and yeast suspension was passed through the cell disrupter at 75 ml/min. The resulting yeast extract was centrifuged at 10,000 rpm for 1 hour in a RC5B centrifuge (Dupont, Wilmington, Del.) in a SLA-3000 rotor. The supernatant was collected.

Example 20
Heterotrimeric Formation of the Human Procollagen Produced in a Fermenter Yeast extract supernatant from strain GYT3681 was treated with pepsin at increasing temperatures, run on SDS-PAGE, and stained as described in Example 9. Both chains of the heterotrimeric collagen in the yeast extract showed resistance to pepsin digestion up to 38° C. A control sample of procollagen isolated from the media of human skin fibroblasts (CRL 1475; ATCC, Rockville, Md.) showed pepsin resistance to 34° C. under identical assay conditions. This experiment indicates the procollagen polypeptides are in the correct heterotrimeric triple helical structure and are stable to >38° C. due the hydroxylation of proline residues within the triple helical region of the procollagen molecule.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making a mammalian collagen or procollagen in yeast, the method comprising the steps of:
   (a) incubating a yeast cell comprising:
      (i) a stable genetic construct comprising in opposite orientations, first and second mammalian collagen genes operably linked to a first single divergent heterologous promoter;
      (ii) a prolyl hydroxylase gene;
      (iii) a protein disulfide isomerase gene, wherein the prolyl hydroxylase and protein disulfide isomerase genes are expressed to produce polypeptides that are associated into active proteins during the incubating step, in a medium under conditions wherein the collagen genes are expressed as procollagen chains and the chains secreted in the form of triple helical procollagen; and
   (b) recovering the triple helical procollagen.

2. The method of claim 1, wherein the first single divergent heterologous promoter comprises a GAL1–10 promoter.

3. The method of claim 1, wherein the collagen genes reside on a plasmid or multiple integrants in the cell.

4. The method of claim 1, wherein the prolyl hydroxylase and protein disulfide isomerase genes are integrated into the genome of the yeast.

5. The method of claim 1, wherein the prolyl hydroxylase gene and protein disulfide isomerase genes are operably linked to a second single divergent heterologous promoter.

6. The method of claim 1, wherein the first and second single divergent heterologous promoters consist essentially of the same nucleotide sequence.

7. The method of claim 1, wherein the protein disulfide isomerase gene comprises a heterologous signal sequence.

8. The method of claim 1, wherein the medium comprises one or more supplemental amino acids which are degraded in the cell to α-ketoglutarate sufficient to promote the hydroxylation of the collagen under the conditions.

9. The method of claim 1, wherein the yeast cell is a *Saccharomyces cerevisiae*.

10. The method of claim 1, wherein the mammalian collagen genes are human collagen genes.

11. A method according to claim 1 wherein the procollagen is heterotrimeric.

12. A method according to claim 1 wherein the collagen genes encode different collagen chains.

13. A method for making a mammalian collagen or procollagen in yeast, the method comprising the steps of:
  (a) incubating a yeast cell comprising:
    (i) a stable genetic construct comprising in opposite orientations, first and second mammalian collagen genes operably linked to a first single divergent heterologous promoter;
    (ii) a prolyl hydroxylase gene;
    (iii) a protein disulfide isomerase gene, wherein the prolyl hydroxylase and protein disulfide isomerase genes are expressed to produce polypeptides that are associated into active proteins during the incubating step, in a medium under conditions wherein the collagen genes are expressed as procollagen chains and the chains secreted in the form of triple helical procollagen,
  wherein the yeast cell is *Saccharomyces cerevisiae,* the prolyl hydroxylase and protein disulfide isomerase genes are integrated into the genome of the yeast, the first single divergent heterologous promoter is a GAL1–10 promoter, the collagen genes reside on a plasmid in the yeast, the prolyl hydroxylase gene and protein disulfide isomerase genes are operably linked to a second single divergent heterologous promoter, the first and second single divergent heterologous promoters are the same, and the mammalian collagen genes are human collagen genes; and
  (b) recovering the triple helical procollagen.

14. A method according to claim 13 wherein the procollagen is heterotrimeric.

15. A yeast cell comprising: (i) a stable genetic construct comprising in opposite orientations, first and second mammalian collagen genes operably linked to a first single divergent heterologous promoter; (ii) a prolyl hydroxylase gene; and (iii) a protein disulfide isomerase gene.

16. The cell of claim 15, wherein the first single divergent heterologous promoter comprises a GAL1–10 promoter.

17. The cell of claim 15, wherein the collagen genes reside on a plasmid or multiple integrants in the cell.

18. The cell of claim 15, wherein the prolyl hydroxylase and protein disulfide isomerase genes are integrated into the genome of the yeast.

19. The cell of claim 15, wherein the prolyl hydroxylase gene and protein disulfide isomerase genes are operably linked to a second single divergent heterologous promoter.

20. The cell of claim 15, wherein the first and second single divergent heterologous promoters consist essentially of the same nucleotide sequence.

21. The cell of claim 15, wherein the protein disulfide isomerase gene comprises a heterologous signal sequence.

22. The cell of claim 15, wherein the yeast cell is a *Saccharomyces cerevisiae*.

23. The cell of claim 15, wherein the mammalian collagen genes are human collagen genes.

24. The cell of claim 15, wherein the first single divergent heterologous promoter is a GAL1–10 promoter, the collagen genes reside on a plasmid in the cell, the prolyl hydroxylase and protein disulfide isomerase genes are integrated into the genome of the yeast, the prolyl hydroxylase gene and protein disulfide isomerase genes are operably linked to a second single divergent heterologous promoter, the first and second single divergent heterologous promoters are the same, the protein disulfide isomerase gene comprises a signal sequence heterologous to the protein disulfide isomerase gene, the yeast cell is a *Saccharomyces cerevisiae,* the mammalian collagen genes are human collagen genes.

25. A method according to claim 24 wherein the collagen genes encode different collagen chains.

* * * * *

UNITED STATES PATENT AND TRADEMARK OFFICE
CERTIFICATE OF CORRECTION

PATENT NO.   : 6,472,171 B1
DATED        : October 29, 2002
INVENTOR(S)  : Toman et al.

It is certified that error appears in the above-identified patent and that said Letters Patent is hereby corrected as shown below:

Column 23,
Line 58, -- triple helical -- should be inserted between "mammalian" and "collagen";

Column 24,
Lines 62-63, "in the form of triple helical procollagen" should read -- in the form of the triple helical collagen or procollagen. --;
Line 64, -- collagen or -- should be inserted between "helical" and "procollagen".

Column 25,
Line 17, "hydroxylation of the collagen under the conditions." should read -- hydroxylation of the triple helical collagen or procollagen. --
Line 26, -- triple helical -- should be inserted between "mammalian" and "collagen";
Lines 40-41, "in the form of triple helical procollagen" should read -- in the form of the triple helical collagen or procollagen. --;

Column 26,
Line 6, -- collagen or -- should be inserted between "helical" and "procollagen".

Signed and Sealed this

Eighth Day of April, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 460
<212> TYPE: DNA
<213> ORGANISM: Saccharomyces cerevisiae

<400> SEQUENCE: 1

-continued

```
gaattctaga tgattgattg attgattgta cagtttgttt ttcttaatat ctatttcgat      60
gacttctata tgatattgca ctaacaagaa gatattataa tgcaattgat acaagacaag     120
gagttatttg cttctctttt atatgattct gacaatccat attgcgttgg tagtcttttt     180
tgctggaacg gttcagcgga aaagacgcat cgctcttttt gcttctagaa gaaatgccag     240
caaaagaatc tcttgacagt gactgacagc aaaaatgtct ttttctaact agtaacaagg     300
ctaagatatc agcctgaaat aaagggtggt gaagtaataa ttaaatcatc cgtataaacc     360
tatacacata tatgaggaaa aataatacaa agtgtttta aatacagata catacatgaa      420
catatgcacg tatagcgccc aaatgtcggt aatgggatcc                           460
```

<210> SEQ ID NO 2
<211> LENGTH: 11
<212> TYPE: DNA
<213> ORGANISM: Saccharomyces cerevisiae

<400> SEQUENCE: 2

```
atctagaatt c                                                           11
```

<210> SEQ ID NO 3
<211> LENGTH: 822
<212> TYPE: DNA
<213> ORGANISM: Saccharomyces cerevisiae

<400> SEQUENCE: 3

```
gaattcgaca ggttatcagc aacaacacag tcatatccat tctcaattag ctctaccaca     60
gtgtgtgaac caatgtatcc agcaccacct gtaaccaaaa caattttaga agtactttca    120
ctttgtaact gagctgtcat ttatattgaa ttttcaaaaa ttcttactt tttttttggat    180 ggacgcaaag aagtttaata atcatattac atggcattac caccatatac atatccat     240 acatatccat atctaatctt acttatatgt tgtggaaatg taaagagccc cattatctta    300
gcctaaaaaa accttctctt tggaactttc agtaatacgc ttaactgctc attgctatat    360
tgaagtacgg attagaagcc gccgagcggg tgacagccct ccgaaggaag actctcctcc    420
gtgcgtcctc gtcttcaccg gtcgcgttcc tgaaacgcag atgtgcctcg cgccgcactg    480
ctccgaacaa taaagattct acaatactag cttttatggt tatgaagagg aaaaattggc    540
agtaacctgg ccccacaaac cttcaaatga acgaatcaaa ttaacaacca taggatgata    600
atgcgattag tttttttagcc ttatttctgg ggtaattaat cagcgaagcg atgattttg     660 atctattaac agatatataa atgcaaaaac tgcataacca ctttaactaa tactttcaac    720 atttcggtt tgtattactt cttattcaaa tgtaataaaa gtatcaacaa aaattgtta     780 atataccctct atactttaac gtcaaggaga aaaacggat cc                        822
```

<210> SEQ ID NO 4
<211> LENGTH: 37
<212> TYPE: DNA
<213> ORGANISM: Saccharomyces cerevisiae

<400> SEQUENCE: 4

```
aattgatgac tgagcggccg cagatctctc gagctgc                              37
```

<210> SEQ ID NO 5
<211> LENGTH: 30
<212> TYPE: DNA
<213> ORGANISM: Saccharomyces cerevisiae
```

-continued

```
<400> SEQUENCE: 5
actactgact cgccggcgtc tagagagctc                                    30

<210> SEQ ID NO 6
<211> LENGTH: 87
<212> TYPE: DNA
<213> ORGANISM: Saccharomyces cerevisiae

<400> SEQUENCE: 6
gaattcctcg agcttaagat gatgcttttg caagctttcc ttttcctgct agctggtttt   60
gcagccaaaa taagcgcgga gcccctg                                       87

<210> SEQ ID NO 7
<211> LENGTH: 23
<212> TYPE: PRT
<213> ORGANISM: Saccharomyces cerevisiae

<400> SEQUENCE: 7

Met Met Leu Leu Gln Ala Phe Leu Phe Leu Leu Ala Gly Phe Ala Ala
  1               5                  10                  15

Lys Ile Ser Ala Glu Pro Leu
             20

<210> SEQ ID NO 8
<211> LENGTH: 20
<212> TYPE: DNA
<213> ORGANISM: Saccharomyces cerevisiae

<400> SEQUENCE: 8
aattcgcggc cgctctagag                                               20

<210> SEQ ID NO 9
<211> LENGTH: 20
<212> TYPE: DNA
<213> ORGANISM: Saccharomyces cerevisiae

<400> SEQUENCE: 9
gcgccggcga gatctcctag                                               20

<210> SEQ ID NO 10
<211> LENGTH: 72
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 10
catatcagct ggggcccaga tctatcgatg ctagcctcga ggaattcgga tccttaaggc   60
ggccgcgata tg                                                       72
```